United States Patent [19]
Alderson et al.

[11] Patent Number: 5,925,734
[45] Date of Patent: Jul. 20, 1999

[54] ISOLATED EPSTEIN-BARR VIRUS BZLF2 PROTEINS THAT BIND MHC CLASS II βCHAINS

[75] Inventors: Mark Alderson; Richard J. Armitage, both of Bainbridge Island, Wash.; Jeffrey I. Cohen, Silver Spring, Md.; Michael R. Comeau; Theresa M. Farrah, both of Seattle, Wash.; Lindsey M. Hutt-Fletcher, Kansas City, Mo.; Melanie K. Spriggs, Seattle, Wash.

[73] Assignee: Immunex Corporation, Seattle, Wash.

[21] Appl. No.: 08/936,854

[22] Filed: Sep. 24, 1997

Related U.S. Application Data

[60] Division of application No. 08/430,633, Apr. 28, 1995, Pat. No. 5,726,286, which is a continuation-in-part of application No. 08/235,397, Apr. 28, 1994, abandoned.

[51] Int. Cl.$^6$ .............................. C07K 1/00; C07K 14/00; C12P 21/08
[52] U.S. Cl. ...................... 530/350; 530/387.3; 435/69.3
[58] Field of Search ........................... 435/69.3; 530/300, 530/350, 387.3

[56] References Cited

U.S. PATENT DOCUMENTS 5,116,964   5/1992   Capon et al. .

FOREIGN PATENT DOCUMENTS

A 0 316 170   5/1989   European Pat. Off. .
A 0 325 224   7/1989   European Pat. Off. .
WO 91/08224   6/1991   WIPO .

OTHER PUBLICATIONS

08/107,353 Spriggs et al. Aug. 13, 1993.
08/145,830 Gayle et al. Oct. 29, 1993.
Baer et al., *Nature* 310:207; 1984.
Cohen et al., *Proc. Natl. Acad. Sci. USA* 81:4183, 1984.
Seible et al., *Proc. Natl. Acad. Sci. USA* 60:902, 1986.
Gascoigne et al., *Proc. Natl. Acad. Sci. U.S.A.* 84:2936, 1987.
Fanslow et al., *J. Immunol.* 149:65, 1992.
Noelle et al., *Proc. Natl. Acad. Sci. U.S.A.* 89:6550, 1992.
Hollenbaugh et al., *EMBO J.* 11:4313, 1992.
Marschall et al., *J. Virol.* 63:938, 1989.
Countryman et al., *J. Virol.* 61:3672, 1987.
Epstein–Barr Virus, in *Fields Virology*, Second Edition, 1990.
Li et al., Abstract of presentation at Cold Spring Harbor, Sep. 1994.

*Primary Examiner*—Mary E. Mosher
*Assistant Examiner*—Ali R. Salimi
*Attorney, Agent, or Firm*—Patricia Anne Perkins

[57] ABSTRACT

Isolated viral proteins, and pharmaceutical compositions made therefrom, are disclosed which are capable of binding to a β chain of a Class II Major Histocompatibility Complex antigen, thereby functioning to inhibit an antigen-specific response. The viral proteins also have superantigen-like activity, and inhibit EBV infection.

6 Claims, 7 Drawing Sheets

MVSFKQVR<u>VPLFTAIALVIVLLAYFLP</u>PRVR

↓↓
GGGRVAAAITWVPKPNVEVWPVDPPPVNFN

KTAEQEYGDKEVKLPHWTPTLHTFQVPQNYTK $\chi$                $\phi$    $\theta$
ANCTYCNTREYTFSYKGCCFYFTKKKHTWNGC
                         ------ ß$_1$ ------    ------

$C_1$          $\theta$      $\theta$         $E$    $\chi\theta$
FQACAELYPCTYFYGPTPDILPVVTRNLNAIE
$\alpha_1$ -------                      ---- $\alpha_2$ ---

$\phi\theta G\theta$       $\Omega$    $\phi$   $\chi$    $G$    $\chi$           $E\Omega C_2$
SLWVGVYRVGEGNWTSLDGGTFKVYQIFGSHC
-- ß$_2$ --   --- l$_1$ ----   -- l$_2$ ----     --- l$_4$ ---- -

$\phi$  $\chi$         $G$  $WND$    $C_2$        $\chi$  $C_1$
TYVSKFSTVPVSHHECSFLKPCLCVSQRSNS
- ß$_3$ -     --- ß$_4$ ---      ------ ß$_5$ ------

Figure 1

ISOLATED EPSTEIN-BARR VIRUS BZLF2 PROTEINS THAT BIND MHC CLASS II β CHAINS

CROSS-REFERENCE TO RELATED APPLICATION

This application is a divisional of application Ser. No. 08/430,633file Apr. 28, 1995, now U.S. Pat. No. 5,726,286, which is a continuation-in-part of application Ser. No. 08/235,397, file Apr. 28, 1994, now abondoned.

TECHNICAL FIELD OF THE INVENTION

The present invention relates generally to the field of viral proteins, and more specifically to viral proteins having immunoregulatory activity.

BACKGROUND OF THE INVENTION

Epstein-Barr virus (EBV) is a double-stranded DNA virus with tropism for some epithelial cells and for B lymphocytes. The entire nucleotide sequence of EBV strain B95-8 has been published (Baer et al., *Nature* 310:207; 1984). From this sequence, it was predicted that EBV has 84 major open reading frames (ORFs). Certain EBV ORFs have been identified as encoding specific viral proteins, however, many ORFs have not been associated with specific viral proteins.

Several groups have investigated an ORF present in the Bam H1 Z fragment of EBV, referred to as BZLF2. Cohen et al. (*Proc. Natl. Acad. Sci.* USA 81:4183, 1984) reported that the Bam H1 Z fragment encoded three peptides ranging in size from 77 to 31 kD. Seible et al. (*Proc. Natl. Acad. Sci.* USA 60:902, 1986) detected the presence of a 140 kD protein in EBV-infected cells which they attributed to a BZLF2 ORF. In contrast, Baer et al. predicted an approximate molecular weight of 25 kD for a protein encoded by the BZLF2 ORF.

None of the studies demonstrated the function of the protein they predicted to be encoded in the Bam HI Z fragment, and none of the proteins disclosed in the prior art correlated to any of the proteins known to be present in purified EBV or directly involved in replication of the virus or transformation of cells by EBV. Thus, prior to the present invention, there was a need in the art to establish the actual amino acid sequence and size of a protein encoded by the BZLF2 ORF, and to determine the function of the protein.

SUMMARY OF THE INVENTION

The present invention identifies a protein encoded by an EBV ORF referred to as BZLF2, which binds to β chains of Class II Major Histocompatibilty Complex (MHC) molecules. The present invention also provides a method for identifying and isolating such viral proteins. The viral proteins of the present invention can be used to regulate immune responses in a therapeutic setting; accordingly, pharmaceutical compositions comprising BZLF2 proteins are also provided.

The isolated viral proteins of this invention are similar to C-type lectins, such as the macrophage mannose receptor, the mammalian asialoglycoprotein receptor and the low-affinity IgE receptor reviewed in Drickamer; *Current Opinion in Structural Biology* 3:393, 1993). The present invention specifically provides isolated BZLF2 protein, in soluble form such as in a fusion protein comprising the extracellular region of BZLF2, and an IgG Fc domain or an oligomerizing zipper domain, as well as in native form.

BZLF2 binds Major Histocompatibility Complex (MHC) Class II β chains. MHC Class II complexes are known to be involved in antigen presentation, and in studies performed using the BZLF2 fusion protein, BZLF2 inhibited various antigen specific responses. Specifically, BZLF2 inhibits antigen-specific antibody formation, proliferation of peripheral blood mononuclear cells, and cytotoxic T cell responses. The present invention thus also provides a method of inhibiting undesirable antigen specific responses in a mammal. Such methods of inhibiting undesirable antigen specific responses are useful in preventing or treating autoimmune disease as well as tissue or organ transplant rejection, and in treatment or prevention of allergy or asthma. BZLF2 proteins also exhibit superantigen-like activity, and are useful as superantigens.

The present invention also provides viral proteins expressed as fusion proteins. These and other aspects of the present invention will become evident upon reference to the following detailed description of the invention.

BRIEF DESCRIPTION OF THE DRAWINGS

FIG. 1 represents the amino acid sequence of a BZLF2 protein. A hydrophobic region which may serve as a transmembrane domain or a signal sequence is underlined. A potential cleavage site that would be useful if the hydrophobic region serves as a signal sequence falls between two arrows (↓). Residues which are conserved or similar across various members of the C-type lectin family are marked as follows: θ denotes an aliphatic residue; χ denotes an aliphatic or aromatic residue; Φ denotes an aromatic residue; Ω denotes the carboxylic residues and their amine variants (D, N, E, Q). Additional conserved residues are denoted by the one-letter amino acid code for the amino acid occurring most commonly in C-type lectin proteins, at that position. $C_1$ and $C_2$ denote conserved cysteine residues that are involved in disulphide bonds in other C-type lectin family members; the two residues marked as $C_1$ form one disulphide bond, and the two residues denoted $C_2$ form a second disulphide bond. The tertiary structure of mannose binding protein is shown below the corresponding residues in the BZLF2 protein; α indicates a region that forms an a helix and β indicates the formation of a β strand in a β pleated sheet. The region of the BZLF2 that is most divergent from that of other C-type lectins is a region that forms a loop in mannose binding protein; the residues in this region of the BZLF2 protein are presented in boldface type. This region has been shown to be involved in $Ca^{2+}$-dependent binding of oligosaccharide by mannose binding protein.

As shown in FIG. 4A, BZLF2/Fc completely inhibited the generation of cytolytic T lymphocytes in an MLC; however, the addition of IL-2 reversed the inhibitory effect of BZLF2/Fc (FIG. 4B). FIGS. 4C and 4D represent dose response curves for BZLF2/Fc, demonstrating inhibition of proliferation and inhibition of CTL induction, respectively, in an MLC.

DETAILED DESCRIPTION OF THE INVENTION

Figure 2A:
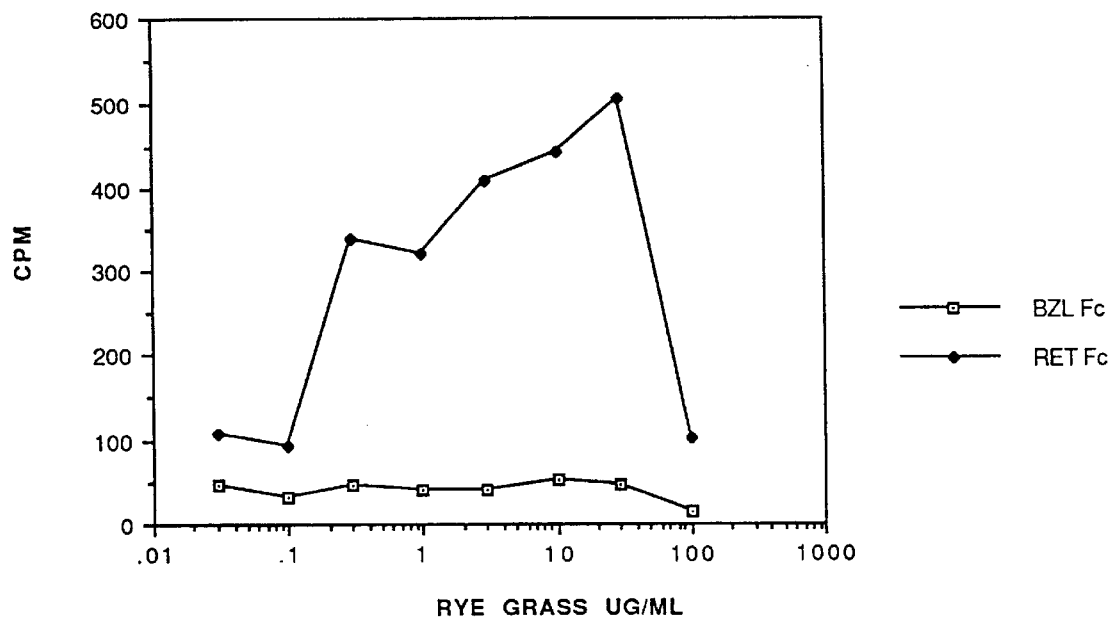
FIGS. 2A–2B illustrates the ability of BZLF2 to inhibit antigen-specific antibody formation in PBMCs from the blood of a donor known to be allergic to rye grass. The results demonstrated that BZLF2/Fc was able to inhibit a secondary, antigen-specific antibody response.

A plasmid containing DNA comprising the BZLF2 ORF was obtained and a soluble BZLF2 protein was expressed in the form of a fusion protein comprising an extracellular region of BZLF2 and a human $IgG_1$ Fc domain. The BZLF2/Fc fusion protein was used in a direct expression cloning technique to isolate a molecule to which BZLF2 binds (referred to as a counterstructure). Nucleotide sequence analysis of the isolated counterstructure indicated that it comprised a β chain of a Class II MHC antigen. Purified BZLF2/Fc was shown to inhibit antigen-specific responses, presumably by binding Class II β chain and interfering with antigen presentation. Additional soluble constructs comprising the extracellular region of BZLF2 can be prepared and are expected to demonstrate the ability to inhibit antigen-specific responses, as does the BZLF2/Fc fusion protein. Moreover, certain soluble constructs of BZLF2 exhibit superantigen-like activity. BZLF2 proteins also inhibit infection and/or transformation of cells by EBV. Additionally, stable transfection of Raji cells (which contain an EBV genome that lacks BZLF2) with a DNA encoding BZLF2 reduced expression of HLA-DR molecules on Raji cells by 50%. A detailed description of the invention and certain technical background information is presented below.

Epstein-Barr Virus

The herpesvirus family comprises enveloped, double stranded DNA viruses which infect various species and exhibit a propensity for establishing latent infections. Epstein-Barr virus (EBV) is a member of the herpesvirus family which infects humans; EBV and related viruses of other species are referred to as lymphocryptoviruses because the latent infections they establish involve lymphoid cells. Primary infection by EBV occurs in the cells of the oropharynx, and frequently results in some level of infection that persists for life, as demonstrated by shedding of virus into saliva. At an early stage of a primary infection, EBV infects B lymphocytes that traffic close to the epithelial basement membrane, transforming the infected B cells and establishing a latent infection. A similar ability to transform B cells can be shown in vitro, wherein EBV infection causes immortalization of the infected B cells.

EBV is endemic in most geographic regions, but is associated with different diseases or syndromes, depending on the locality and the individual infected. In western countries, primary EBV infection usually occurs in childhood. When young adults are infected, they frequently manifest the syndrome known as infectious mononucleosis. Individuals in developing nations tend to become infected at an earlier age, and do not usually develop infectious mononucleosis. In addition to causing infectious mononucleosis, EBV is associated with Burkitt's lymphoma in regions where malaria is endemic, and with nasopharyngeal carcinoma. EBV is also associated with B cell lymphomas that occur in immunocompromnised individuals.

EBV ORFs are identified by an acronym comprising an abbreviation representing the restriction enzyme fragment in which they start translation or transcription, the letter L (leftward) or R (rightward) indicating the orientation of the ORF, the letter F indicating a reading frame, and a numerical designation. For example, the membrane proteins gp350/200 are encoded in the Bam HI fragment L, have a leftward orientation, and are encoded by RNAs derived from the first ORF, or BLLF1a and BLLF1b. The present invention relates to a protein encoded by an EBV ORF present on the Bam H1 Z fragment, which is referred to as BZLF2.

BZLF2 ORF

In a mapping study utilizing hybrid selection and in vitro translation of RNA from cells productively infected with EBV, Cohen et al. (supra) demonstrated that the Bam H1 Z fragment encoded three polypeptides ranging in size from 77 to 31 kD. Seible et al. (supra) also used hybrid selection to analyze proteins expressed from the Bain HI Z fragment of EBV. They detected the presence of a 140 kD protein in EBV-infected cells, using anti-serum specific for a fusion protein encoded by the BZLF2 fragment. They concluded the size of the protein, which was much larger than predicted, was presumably due to RNA splicing, which is known to occur in other genes during replication of EBV. In contrast, Baer et al. (supra) predicted an approximate molecular weight of 25 kD for a protein encoded by the BZLF2 ORF. None of the investigators identified a known viral protein as being encoded by the BZLF2 ORF, nor was a protein structure or function known.

Our analysis of the predicted protein product of the BZLF2 ORF taught by Baer et al. (supra) indicates that it is a likely member of the C-type lectin family, a group of proteins exhibiting a conserved domain referred to as a C-type lectin domain. A typical C-type lectin domain consists of about 110 to 130 amino acids, and includes four conserved cysteines which are involved in the formation of two intrachain disulfide bonds. The C-type lectin domain is found in type II membrane proteins such as asialoglycoprotein receptors, low affinity IgE receptors, Kupffer cell receptor and a number of distantly related proteins expressed on the surface of lymphoid cells (NKG2, NKR-P1, YE1/8, CD72, and LyB-2). Collectins such as mannose-binding protein, pulmonary surfactant-associated protein and conglutinin are exemplary soluble proteins comprising a CTL domain. The C-type lectin domain often functions as a calcium-dependent carbohydrate recognition domain.

Computer searches of the Genbank database, release 76 (April 1993) using the GCG implementation of TFasta (Genetics Computer Group, 1991; *Program Manual for the GCG Package*, Version 7, April 1991; University of Wisconsin Genetics Computer Group, Madison, Wis.) indicate a high degree of sequence similarity between BZLF2 and several members of the C-type lectin family of proteins. BZLF2 has the characteristic four conserved cysteines, and a sequence very similar to the "WIGL" motif present in the C-type lectin family ("WVGV" in BZLF2). A hydrophobic region at the N-terminus of the predicted BZLF2 protein could serve either as a signal peptide, or as a transmembrane domain. However, despite its similarities, the predicted amino acid sequence of BZLF2 diverges significantly from that of classic C-type lectins.

The structure of one member of the C-type lectin family, mannose binding protein, in complex with its ligand, has been determined (Weis et al., *Nature* 360:127, 1992; Weis et al., *Science* 254:1608, 1991). It is a mixed alpha-beta structure (two α-helix-forming regions and five regions that form β-pleated sheets), with an extensive loop region. The loop region, in conjunction with the fourth beta strand ($\beta_4$), is involved in $Ca^{2+}$-dependent oligosaccharide binding. BZLF2 shares certain structural similarities with the classic members of the C-type lectin family. However, it appears to differ in function in that it can bind its counterstructure (MHC Class II β clain) in the absence of calcium. The MHC Class II β chain carries only a single oligosaccharide residue; moreover, BZLF2 binds a non-glycoylated form of recombinant MHC Class II β chain. Thus, BZLF2 also differs from classic C-type lectins in that it does not bind to carbohydrate moieties.

As described herein, a full length BZLF2 protein was expressed, tested, and found to act as a superantigen. In contrast, an BZLF2 deletion mutant that was missing the amino terminal 33 amino acids, and which was expressed in the form of an immunoglobulin Fc fusion protein, bound MHC Class II molecules and inhibited antigen presentation. BZLF2 proteins will thus be useful regulating an immune responses in a therapeutic setting. BZLF2 proteins that bind Class II molecules but that do not act as superantigens (BZLF2 Class II binding proteins) are useful in inhibiting undesirable antigen specific responses in a mammal, for example, in preventing or treating autoimmune disease as well as tissue or organ transplant rejection, and in treatment or prevention of allergy or asthma.

BZLF2 proteins that bind Class II molecules and act as superantigens (BZLF2 Class II superantigen proteins) have utility in therapeutic regimens that require activation of a broad spectrum of T cells (as opposed to antigen-specific activation). Moreover, fusion proteins comprising BZLF2 superantigen proteins and a heterologous protein that specifically binds to malignant cells will also be useful in treating cancer and viral disease in which viral antigens are expressed on host cells. For example, a fusion protein of staphylococcal enterotoxin A and a monoclonal antibody specific for human colon carcinoma cells, C215, inhibited tumor growth and allowed long-term survival of mice carrying B16 melanoma cells (Dohlstein et al., *Proc. Natl. Acad. Sci*, USA 91:8845; 1994). Such useful fusion proteins can comprise antibodies, or molecules that specifically bind receptor or ligand proteins found on malignant cells (i.e., CD30), or that specifically bind to viral proteins. Furthermore, superantigens that functionally inactivate and delete certain peripheral T cells will also be useful in treating autoimmune conditions (see Kim et al., *J. Exp. Med.* 174:1431, 1991).

MHC Class II antigens

Antigen presenting cells (APC), which include mononuclear phagocytes, certain dendritic cells such as Langerhans dendritic cells and follicular dendritic cells, and B cells, take up proteinaceous antigens and process them. Such processing can involve unfolding the protein or fragmentation (enzymatic and/or chemical) into smaller peptides. Processed antigens are then presented on the surface of the APC, in the form of a complex with the class II molecule. CD4+T cells respond to APC bearing such antigen/class II complexes by proliferating and secreting lymphokines (including Interleukin-2 and Interferon-γ). Class II molecules are thus central to both the humoral and cellular branches of an immune response.

Peptide antigens bind to Class II molecules with varying affinity, and failure to respond to certain peptide antigens has been associated with the inability of particular Class II molecules to bind the peptide. The original identification of these molecules came from the discovery that allelic variations within the regions encoding MHC Class I (HLA–D region in humans and H-2I region in the mouse) resulted in stimulation in mixed lymphocyte cultures (MLC) in vitro, and led to graft rejections in vivo.

Class II antigens are composed of two non-covalently associated polypeptide chains designated α and β. The a chain is an acidic polypeptide with two external, structural domains and an approximate molecular weight of 25–33 kD. The β chain is a basic polypeptide of 24–29 kD in molecular weight, and also has two external structural domains. Both chains are glycosylated transmembrane proteins and contain a highly conserved region of ten to twelve peptides linking the membrane proximal domain to the hydrophobic transmembrane region. The higher molecular weight of the a chain is generally accounted for by the presence of two carbohydrate moieties, a complex type oligosaccharide and a high mannose type. The β chain contains a single complex type carbohydrate.

Additional information regarding the structure and function of MHC Class II antigens may be found in many general immunology textbooks (for example, *Fundamental Immunoloy*, Second Edition; W. E. Paul, Ed. Raven Press, 1993), as well as in descriptions of the numerous scientific studies that have been performed.

Superantigens

Superantigens bind to class II MHC molecules and to T cell receptors for antigens (TCR), cross-linking cells expressing MHC class II to cells expressing TCR. Binding to the TCR occurs through the variable region of the β chain of the TCR, referred to as Vβ. Unlike conventional antigens, superantigens do not require intracellular processing by antigen presenting cells in order to bind MHC class II. Superantigens also differ from conventional antigens in binding to a region of a class II molecule at a site other than the antigen binding cleft.

The proportion of T cells that proliferate in response to a superantigen can range from 5 to 25% of the T cells that encounter the superantigen. The high frequency of activation is accounted for by the binding of the superantigen to the Vβ region; virtually all T cells bearing a particular Vβ are activated upon binding of an appropriate superantigen. In contrast, for a primary antigen response against a particular (non-superantigen) foreign antigen, a markedly lower proportion of T cells responds, from about one in $10^4$ to one in $10^6$ T cells.

One type of superantigen, the minor lymphocyte stimulating (Mls) determinants, was first detected by the stimulation of a strong primary mixed-lymphocyte reaction between cells from mice of the same MHC haplotype. The Mls genes caused deletion of T cells that expressed certain Vβ chains (Kappler et al., *Nature* 332:35, 1988; MacDonald et al., *Nature* 332:40, 1988). Subsequent studies demonstrated that Mls determinants are actually encoded by an ORF of the 3' long terminal repeat of the MMTV genome (Choi et al., supra). A review of the various Mls determinants is presented by Acha-Orbea, *Immunol. Today* 12:357, 1991.

Bacterial superantigens include the Staphylococcal enterotoxins (SE) and toxic shock syndrome toxin (TSST-1), *Streptococcus pyogenes* exotoxins (SPE-A, SPE-C, pep M5 and exfoliating toxin), and *Pseudomonas aeruginosa* exotoxin A. Other bacteria also produce toxins that appear to act as superantigens, including *Yersinia enterocolitica, Clostridium perfringens* and *Mycobacterium* spp. Rabies virus is also believed to encode a superantigen (Lafon et al., *Nature* 358:507, 1992), as is Moloney murine leukemia virus (Huigin et al., *Science* 252:424, 191). Several lines of evidence also indicate that a superantigen may be encoded by the Human Immunodeficiency Virus, and may be implicated in AIDS (reviewed in Irwin and Gascoigne, *J. Leukocyte Biol.* 54:495; 1993).

The ability of superantigens to stimulate clonal deletion of T cells based on the Vβ expressed has stimulated study of the role of superantigens in self-tolerance, and in anergy (reviewed in Marrack et al., *Inmunol. Rev.* 133:119, 1993; MacDonald et al., *Immunol. Rev.* 133:105, 1993; Herman et al., *Annu. Rev. Immunol.* 9:745, 1991). Bacterial superantigens may cause some of the symptoms of food poisoning by activating macrophages or T cells (Johnson et al., *FASEB J.* 5:2706, 1991; Marrack et al., *J. Exp. Med.* 171:455, 1990). Furthermore, certain autoimmune diseases exhibit characteristics that implicate superantigens in their etiology (reviewed in Irwin and Gascoigne, supra).

Proteins and Analogs

The present invention provides isolated BZLF2 proteins having inmmunoregulatory activity. Such proteins are substantially free of contaminating endogenous materials and, optionally, without associated native-pattern glycosylation. Derivatives of the BZLF2 proteins within the scope of the invention also include various structural forms of the primary protein which retain biological activity. Due to the presence of ionizable amino and carboxyl groups, for example, a BZLF2 protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Other derivatives of the BZLF2 protein within the scope of this invention include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of BZLF2 proteins (e.g., poly-His). The amino acid sequence of the viral proteins can also be linked to an identification peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*.

Fusion proteins further comprise the amino acid sequence of a BZLF2 protein linked to an immunoglobulin Fc region. An exemplary Fc region is a human IgG1 having a nucleotide and amino acid sequence set forth in SEQ ID NO:4. Fragments of an Fc region may also be used, as can Fc muteins such as those described in USSN 08/145,830, filed Oct. 29, 1993. Depending on the portion of the Fc region used, a BZLF2 protein may be expressed as a dimer, through formation of interchain disulfide bonds. If BZLF2 fusion proteins are made with both heavy and light chains of an antibody, it is possible to form a viral protein oligomer with as many as four BZLF2 protein regions.

In another embodiment, BZLF2 proteins further comprise an oligomering zipper domain. Oligomerizing zipper domains are described in U.S. Ser. No. 08/107,353, filed Aug. 13, 1993, the relevant disclosure of which is incorporated by reference herein. Examples of leucine zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., *Science* 245:646, 1989; Turner and Tjian, *Science* 243:1689, 1989), and the gene product of the murine proto-oncogene, c-myc (Landschulz et al., *Science* 240:1759, 1988). The fusogenic proteins of several different viruses, including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990). Preferred oligomerizing zipper domains are represented in SEQ ID NOs:6 and 7; the zipper represented by SEQ ID NO:7 forms a homodimer.

BZLF2 protein derivatives may also be used as immunogens, reagents in immunoassays, or as binding agents for affinity purification procedures, for example, in purifying MHC Class II β chain. BZLF2 protein derivatives may also be obtained by cross-linking agents, such as M-maleimidobenzoyl succinimide ester and N-hydroxysuccinimide, at cysteine and lysine residues. BZLF2 proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the BZLF2 protein or against other proteins which are similar to the viral protein.

The present invention also includes BZLF2 proteins with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of BZLF2 DNAs in bacteria such as *E. coli* provides non-glycosylated molecules. Functional mutant analogs of BZLF2 protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

BZLF2 protein derivatives may also be obtained by mutations of the native viral proteins or its subunits. A BZLF2 mutated protein, as referred to herein, is a polypeptide homologous to a BZLF2 protein but which has an amino acid sequence different from the native viral protein because of one or a plurality of deletions, insertions or substitutions. The effect of any mutation made in a DNA encoding a BZLF2 peptide may be easily determined by analyzing the ability of the mutated BZLF2 peptide to bind its counter structure, MHC Class II β chain.

Bioequivalent analogs of viral proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered. Subunits of viral proteins may be constructed by deleting terminal or internal residues or sequences. Additional guidance as to the types of mutations that can be made is provided by a comparison of the sequence of BZLF2 to the sequences and structures of other C-type lectin family members.

Mutations in nucleotide sequences constructed for expression of analog BZLF2 proteins must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated viral proteins screened for the desired activity.

Not all mutations in the nucleotide sequence which encodes a viral protein will be expressed in the final product, for example, nucleotide substitutions may be made to enhance expression, primarily to avoid secondary structure loops in the transcribed MRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Due to code degeneracy, there can be considerable variation in nucleotide sequences encoding the same amino acid sequence. Other embodiments include sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding BZLF2 proteins, and other sequences which are degenerate to those which encode the BZLF2 proteins.

Expression of Recombinant BZLF2 Proteins

The proteins of the present invention are preferably produced by recombinant DNA methods by inserting a DNA sequence encoding BZLF2 protein into a recombinant expression vector and expressing the DNA sequence in a recombinant microbial expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding BZLF2 proteins or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding BZLF2 proteins which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ P$_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., Cell 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of BZLF2 protein DNA is referred to as pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the BZLF2 proteins of the present invention. Transformed host cells may express the desired BZLF2 protein, but host cells transformed for purposes of cloning or amplifying viral DNA do not need to express the BZLF2 protein. Expressed BZLF2 proteins will preferably be secreted into the culture supernatant, depending on the DNA selected, but may be deposited in the cell membrane.

Suitable host cells for expression of viral proteins include prokaryotes, yeast or higher eukaryotic cells under the control of appropriate promoters. Prokaryotes include gram negative or gram positive organisms, for example *E. coli* or Bacillus spp. Higher eukaryotic cells include established cell lines of mammalian origin as described below. Cell-free translation systems could also be employed to produce viral proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, N.Y. 1985), the relevant disclosure of which is hereby incorporated by reference.

Prokaryotic expression hosts may be used for expression of BZLF2 proteins that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Recombinant BZLF2 proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding the viral protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci.* USA 75:1929, 1978, selecting for Trp⁺ transformants in a selective medium consisting of 0.67% yeast nitrogen base, 0.5% casamino acids, 2% glucose, 10 μg/ml adenine and 20 μg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-l/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of BZLF2 proteins

Purified BZLF2 proteins or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Aricon or Millipore Pellicon ultrafiltration unit.

Following the concentration step, the concentrate can be applied to a suitable purification matrix. For example, a suitable affinity matrix can comprise a counter structure protein (i.e. MHC Class II β chain) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying BZLF2.

Affinity chromatography is a particularly preferred method of purifying BZLF2 proteins. For example, a BZLF2 protein expressed as a fusion protein comprising an immunoglobulin Fc region can be purified using Protein A or Protein G affinity chromatography. Moreover, a BZLF2 protein comprising an oligomerizing zipper domain may be purified on a resin comprising an antibody specific to the oligomerizing zipper domain. Monoclonal antibodies against the BZLF2 protein may also be useful in affinity chromatography purification, by utilizing methods that are well-known in the art.

Finally, one or more reversed-phase high performance liquid chromatography (RP-HPLC) steps employing hydrophobic RP-HPLC media, e.g., silica gel having pendant methyl or other aliphatic groups, can be employed to further purify a viral protein composition. Some or all of the foregoing purification steps, in various combinations, can also be employed to provide a homogeneous recombinant protein.

Recombinant BZLF2 protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant viral protein can be disrupted by any convenient method, including freeze-thaw cycling, sonication, mechanical disruption, or use of cell lysing agents.

Fermentation of yeast which express viral protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Viral protein synthesized in recombinant culture is characterized by the presence of non-viral cell components, including proteins, in amounts and of a character which depend upon the purification steps taken to recover the viral protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of BZLF2 protein free of other proteins which may be normally associated with the BZLF2 protein as it is found in nature in its species of origin.

Administration of BZLF2 Protein Compositions

The present invention provides methods of using therapeutic compositions comprising an effective amount of a viral protein and a suitable diluent and carrier, and methods for regulating an immune response. Also provided are methods of inhibitng EBV infection by admninstering BZLF2 proteins. The use of BZLF2 proteins in conjunction with soluble cytokine receptors or cytokines, or other imunoregulatory molecules is also contemplated.

For therapeutic use, purified BZLF2 protein is administered to a patient, preferably a human, for treatment in a manner appropriate to the indication. Thus, for example, BZLF2 protein compositions administered to suppress immune function can be given by bolus injection, continuous infusion, sustained release from implants, or other suitable technique. Typically, a therapeutic agent will be administered in the form of a composition comprising purified BZLF2 protein in conjunction with physiologically acceptable carriers, excipients or diluents. Such carriers will be nontoxic to recipients at the dosages and concentrations employed.

Ordinarily, the preparation of such BZLF2 protein compositions entails combining the viral protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

BZLF2 proteins are administered for the purpose of preventing or inhibiting undesirable, antigen-specific immune or inflammatory responses. Exemplary conditions in which it is advantageous to inhibit such undesirable responses include autoimmune syndromes, including myasthenia gravis, multiple sclerosis and systemic lupus erythematosis, and others as described in U.S. Pat. No. 5,284,935. Antibodies to the murine equivalent of MHC Class II antigens have been shown to provide protection against development of autoimmune syndromes in various animal models (Sriram and Steinman, *J. Exp. Med.* 158:1362, 1983; Steinman et al., *Proc. Natl. Acad. Sci.* USA 78:111, 1981; Waldor et al., *Proc. Natl. Acad. Sci.* USA 80:2713, 1983). Moreover, BZLF2 compositions can also be useful to prevent or treat rejection of tissue and/or organ transplants. Other conditions for which BZLF2 compositions can be useful include those which involve undesirable immune responses to foreign antigens, for example those which occur in allergy or asthma.

BZLF2 proteins can also be administered for the purpose of acting as a superantigen, for example, in order to control disease activity in autoimmune syndromes. Injection of bacterial superantigen SEB into autoimmune MRL/lpr mice suppressed disease activity in a dose-0dependent manner (Kim et al., *J. Exp. Med.* 174:1431; 1991). BZLF2 superantigens also have utility in therapeutic regimens that require activation of a broad spectrum of T cells, and fusion proteins comprising BZLF2 superantigen proteins and a heterologous protein that specifically binds to malignant cells will also be useful in treating cancer and viral disease in which viral antigens are expressed on host cells.

Moreover, BZLF2 proteins inhibit EBV infection of cells. Thus, BZLF2 proteins an also be administered to prevent or treat EBV infection in an individual. EBV is associated with infectious mononucleosis, Burkitt's lymphoma (in regions where malaria is endemic), nasopharyngeal carcinoma, and B cell lymphomas that occur in immunocompromised individuals. EBV also causes severe, often fatal infections in males with X-linked lymphoproliferative syndrome. BZLF2 proteins will thus be useful in preventing or treating these and other conditions caused by EBV.

Preparation of Fusion Proteins Comprising Viral Proteins

Soluble forms of some mammalian proteins have been expressed as fusion proteins in which an extracellular domain of a membrane protein is joined to an immunoglobulin heavy chain constant (Fc) domain (Gascoigne et al., *Proc. Natl. Acad. Sci.* U.S.A. 84:2936, 1987; Sledziewski et al., European patent application 89100787.4, publication number 0 325 224, published Jul. 26, 1989; Fanslow et al., *J. Immunol.* 149:65, 1992; Noelle et al., *Proc. Natl. Acad. Sci.* U.S.A. 89:6550, 1992; Capon et al., U.S. Pat. No. 5,116,964, issued May 26, 1992; U.S. Ser. No. 07/969,703, filed Oct. 23, 1992; U.S. Ser. No. 07/966,775, filed Oct. 27, 1992; U.S. Ser. No. 07/977,693, filed Nov, 13, 1992; U.S. Ser. No. 08/097,827, filed Jul. 23, 1993; U.S. Ser. No. 08/106,507, filed Aug. 13, 1993; U.S. Ser. No. 08/111,758, filed Aug. 25, 1993; and U.S. Ser. No. 08/114,426, filed Aug. 30, 1993), or with an extracellular domain of murine T lymphocyte antigen CD8 (Hollenbaugh et al., *EMBO J.* 11:4313, 1992). Such fusion proteins are useful as reagents to detect their cognate proteins. They are also useful as therapeutic agents in treatment of disease. Mutated Fc regions have also been used to prepare soluble forms of transmembrane proteins. Useful Fc muteins (mutated proteins) are described in U.S. Ser. No. 08/145,830, filed Oct. 29, 93, the relevant disclosure of which is hereby incorporated by reference.

Oligomerizing zipper is a term that is used to refer to a repetitive heptad motif containing four to five leucine residues present as a conserved domain in several proteins. Oligomerizing zippers fold as short, parallel coiled coils, and are believed to be responsible for oligomerization of the proteins of which they form a domain. Sequences derived from the fos and jun leucine zippers have been used in the formation of bispecific antibodies by expression of DNA encoding the $V_L$ and $V_H$ regions of antibodies as fusion proteins with the leucine zipper sequences. (Kostelny et al., *J. Immunol.* 148:1547, 1992) Leucine zipper sequences have also been used to replace the dimerization domain of λ repressor, a soluble DNA-binding protein of bacteriophage λ (Hu et al., *Science* 250:1400, 1990), and in the preparation of a dimeric form of MalE, a maltose binding protein of *E. coli* that is exported into the periplasmic space (Blondel and Bedoulle, *Protein Engineering* 4:457, 1991). Oligomerizing zippers are described in U.S. Ser. No. 08/107,353, filed Aug. 13, 1993.

Fusion proteins comprising viral proteins may also be prepared. In addition to a viral protein, such fusion proteins will also comprise a fusion moiety such as an oligomerizing zipper or an immunoglobulin Fc region, as described above. The BZLF2/Fc and BZLF2/oligomerizing zipper proteins described in great detail herein are exemplary of soluble viral fusion proteins. Other exemplary viral proteins that will be useful in forming such soluble fusion proteins include poxvirus proteins such as T2, described in U.S. Ser. No. 07/963,330, filed Oct. 19, 1992; A53R, described in U.S. Ser. No. 08/089,458, filed Jul. 20, 1993; and two vaccinia virus proteins structurally related to the Interleukin-1 receptor (Smith and Chan, *J. Gen. Virol.* 72:511; 1991). Additional poxvirus proteins may also be prepared; see for example Johnson et al. (*Virology* 196:381; 1993) which discusses the known ORFs of vaccinia virus. Moreover, proteins encoded by other viruses such as EBV and other members of the Herpesvirus family are included among viral proteins which can form soluble fusion proteins.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes construction of a BZLF2/Fc DNA construct to express a soluble BZLF2-immunoglobulin Fc fusion protein referred to as BZLF2/Fc. DNA encoding BZLF2/Fc comprises sequences encoding a leader (or signal) peptide (murine IL-7 leader, SEQ ID NO:3; Namen et al., *Nature* 333:571, 1988), an octapeptide referred to as Flag® (SEQ ID NO:3; Hopp et al., supra), a suitable Fc region of an immunoglobulin (SEQ ID NO:4; U.S. Ser. No. 07/969,703, filed Oct. 23, 1992), a flexible linker sequence (SEQ ID NO:5, or as described in U.S. Pat. No. 5,073,627, issued Dec. 17, 1991) and the extracellular region of BZLF2 from amino acid 34 to amino acid 223 (SEQ ID NO:1). An expression vector containing a leader sequence, and human $IgG_1$ Fc lacking approximately 30 amino acids from the C terminal is prepared using conventional techniques of enzyme cutting and ligation of fragments encoding a leader sequence, and the truncated human $IgG_1$ Fc. Deletion of the C terminal region of the IgG$_1$ Fc results in inability of the expressed protein to bind Protein A/G. The resulting vector is then restricted with Nsi 1 and Not 1. The 3' end of the IgG$_1$ Fc is subsequently reconstructed from the Nsi 1 site to include a flexible linker sequence, as part of a three-way ligation as described below.

A PCR technique (Saiki et al., *Science* 239:487, 1988) was employed using 5' (upstream) and 3' (downstream) oligonucleotide primers to amplify the DNA sequences encoding BZLF2 extracellular ligand binding domain from a cosmid containing the portion of Epstein-Barr virus genome that encompasses the Bam HI Z fragment (J. Virol. 67:7298; 1993) which contains the BZLF2 ORF, to form a PCR fragment. The upstream oligonucleotide primer introduced a Spe 1 site upstream from the extracellular domain of BZLF2 (amino acids 34 through 223 of SEQ ID NO:1). A downstream oligonucleotide primer introduced a Not 1 site just downstream of the termination codon of the BZLF2. The PCR fragment was then ligated into the expression vector containing a leader sequence, and truncated human IgG$_1$ Fc in a three-way ligation including a Nsi 1 to Spe 1 fragment that reconstructed the C-terminal region of the human IgG$_1$ Fc and included the flexible linker sequence. The resultant DNA construct (BZLF2/Fc) was transfected into the monkey kidney cell line CV-1/EBNA (ATCC CRL 10478). The construct encoded a soluble BZLF2/Fc protein which was purified by affinity chromatography.

Large scale cultures of CV-1/EBNA cells transfected with the construct encoding BZLF2/Fc were grown to accumulate supernatant containing BZLF2/Fc. The CV-1/EBNA cell line permits expression of recombinant proteins ligated into the pCD406 vector and other vectors containing the EBV origin of replication. The BZLF2 IFc fusion protein in supernatant fluid was purified by affinity purification. Briefly, culture supernatant containing the BZLF2/Fc fusion protein was purified by filtering mammalian cell supernatants (e.g., in a 0.45$\mu$ filter) and applying filtrate to an antibody affinity column comprising biotinylated goat anti-human IgG (Jackson Immunoresearch Laboratories, Inc., Westgrove, Pa, USA) coupled to Streptavidin-agarose (Pierce Chemical, Rockford, Il, USA) at 4° C., at a flow rate of approximately 60 to 80 ml/hr for a 1.5 cm×12.0 cm column. The column was washed with approximately 20 column volumes of PBS (phosphate buffered saline), until free protein could not be detected in wash buffer. Bound fusion protein was eluted from the column with 12.5 mM citrate buffer, 75 mM NaCl, pH 2.8, and brought to pH 7 with 500 mM Hepes buffer, pH 9.1.

The purified BZLF2/Fc peptide was used to screen peripheral blood T cells and T-cell clonal lines for expression of a counterstructure by FACS analysis. Briefly, cells were incubated with BZLF2/Fc protein (5 ig/ml), then washed to remove unbound BZLF2 /Fc. Biotin-labeled goat anti-human IgG antibody (Jackson Labs, Bar Harbor, ME) was added as the second step reagent. Binding of BZLF2/Fc was detected by the addition of streptavidin-phycoerythrin.

EXAMPLE 2

This example describes the direct expression cloning of human MHC Class II β chain using BZLF2/Fc. The purified, oligomeric BZLF2/Fc peptide was used to screen a human T-cell PL-1 clone library for expression of a counter structure substantially as described by using a modified slide autoradiographic technique, substantially as described by Gearing et al., EMBO J. 8:3667, 1989.

Briefly, a cDNA library was constructed by reverse transcription of poly (A)+mRNA isolated from the total RNA extracted from the PL-1 cell line, described in U.S. Ser. No. 08/060,843, file May 7, 1993. The library construction technique was substantially similar to that described by Ausubel et al., eds., *Current Protocols In Moleciular Biology*, Vol. 1, (1987). Poly (A)+mRNA was isolated by oligo dT cellulose chromatography and double-stranded cDNA was made substantially as described by Gubler et al., *Gene* 25:263, 1983. Poly(A)$^+$ mRNA fragments were converted to RNA-cDNA hybrids by reverse transcriptase using random hexanucleotides as primers. The RNA-cDNA hybrids were then converted into double-stranded cDNA fragments using RNAase H in combination with DNA polymerase I. The resulting double-stranded cDNA was blunt-ended with T4 DNA polymerase.

Bgl 2 adaptors were ligated to 5' ends of resulting blunt-ended cDNA, as described in Haymerle et al., *Nucleic Acids Res.* 14:8615, 1986. Non-ligated adaptors were removed by gel filtration chromatography at 68° C. This left 24 nucleotide non-self-complementary overhangs on cDNA. The same procedure was used to convert 5' Bgl 2 ends of the mammalian expression vector pDC406 to 24 nucleotide overhangs complementary to those added to cDNA. Optimal proportions of adaptored vector and cDNA were ligated in the presence of T4 polynucleotide kinase. Dialyzed ligation mixtures were electroporated into *E. coli* strain DH5α and transformants selected on ampicillin plates.

Plasmid DNA was isolated from pools consisting of approximately 2,000 clones of transformed *E. coli* per pool. The isolated DNA was transfected into a sub-confluent layer of CV1-EBNA cells using DEAE-dextran followed by chloroquine treatment substantially according to the procedures described in Luthman et al., *Nitcl. Acids Res.* 11: 1295, 1983 and McCutchan et al., *J. Natl. Cancer Inst.* 41:351, 1986.

CV1-EBNA cells were maintained in complete medium (Dulbecco's modified Eagles' media containing 10% (v/v fetal calf serum, 50 U/ml penicillin, 50 U/ml streptomycin, and 2 mM L-glutamine) and were plated to a density of approximately 2×10$^5$ cells/well in single-well chambered slides (Lab-Tek). The slides were pre-treated with 1 ml fibronectin-like engineered protein polymer (10 $\mu$g/ml PBS) for two hours followed by a single washing with PBS. Media was removed from adherent cells growing in a layer and replaced with 1.8 ml complete medium containing 66.6 $\mu$M chloroquine sulfate. About 0.2 ml of a DNA solution (2 $\mu$g DNA, 0.5 mg/ml DEAE-dextran in complete medium containing chloroquine) was added to the cells and the mixture was incubated at 37° C. for about five hours. Following incubation, media was removed and the cells were shocked by addition of complete medium containing 10% DMSO (dimethylsulfoxide) for 2.5–20 minutes. Shocking was followed by replacement of the solution with fresh complete medium. The cells were grown in culture for two to three days to permit transient expression of the inserted DNA sequences. These conditions led to a 30% to 80% transfection frequency in surviving CV1-EBNA cells.

After 48–72 hours, transfected monolayers of CVI-EBNA cells were assayed by slide autoradiography for expression of BZLF2 counterstructure, using a method similar to that of Gearing et al., supra. BZLF2/Fc fusion protein is prepared as described in Example 1. Transfected CV1-EBNA cells were washed once with binding medium (RPMI 1640 containing 25 mg/mi bovine serum albumin (BSA), 2 mg/ml sodium azide, 20 mM Hepes pH 7.2, and 50 mg/ml nonfat dry milk) and incubated for 2 hours at 4° C. in binding medium containing 1 $\mu$g/ml BZLF2/Fc protein. Cells were washed to remove unbound BZLF2/Fc protein, and approximately 1–2×10$^{-9}$M $^{125}$I-mouse anti-human Fc F(ab) was added.

After incubation, cells in the chambered slides were washed three times with binding buffer, followed by two washes with PBS (pH 7.3) to remove unbound radiolabeled F(ab) fragments.

The cells were fixed by incubating in 10% gluteraldehyde in PBS (30 minutes at room temperature), washed twice in PBS and air-dried. The slides were dipped in Kodak GTNB-2 photographic emulsion (6×dilution in water) and exposed in the dark for two to four days at room temperature in a light-proof box. The slides were developed in Kodak D19 developer, rinsed in water and fixed in Agfa G433C fixer. The slides were individually examined under a microscope at 25–40×magnification. Positive slides showing cells expressing BZLF2 counterstructure were identified by the presence of autoradiographic silver grains against a light background.

One pool containing approximately 2000 individual clones was identified as potentially positive for binding the BZLF2/Fc fusion protein. The pool was titered and plated to provide plates containing approximately 200 colonies each. Each plate was scraped to provide pooled plasmid DNA for transfection into CVl-EBNA cells according to the same procedure described above. The smaller pools were screened by slide autoradiography as described previously. One of the smaller pools contained clones that were positive for BZLF2 counterstructure as indicated by the presence of an expressed gene product capable of binding to the BZLF2/Fc fusion protein.

The positive smaller pool was titered and plated to obtain individual colonies. Approximately 396 individual colonies were picked and inoculated into culture medium in individual wells of 96-well plates. Cultures were mixed by pooling rows and columns and the mixed cultures were used to prepare DNA for a final round of transfection and screening. An intersection of a positive row and a positive column indicated a potential positive colony. Twelve potential positive colonies (i.e., candidate clones) were identified. DNA was isolated from each candidate clone, retransfected and rescreened. Five candidate clones were positive by binding to BZLF2/Fc. The nucleotide sequence of the BZLF2 counterstructure was determined by dideoxynucleotide sequencing, and was shown to be the nucleotide sequence of a human MHC class II β chain (for review, see Kaufman et al., *Cell* 36:1, 1984).

EXAMPLE 3

This example describes construction of a BZLF2 DNA construct to express a soluble BZLF2 fusion protein referred to as trimeric BZLF2.Trimeric BZLF2 comprises a leader sequence, and a 33 amino acid sequence referred to as an "oligomerizing zipper" (SEQ ID NO:6; U.S. Ser. No. 07/969,703, filed Oct. 23, 1992), followed by the extracellular region of BZLF2 from amino acid 34 to amino acid 223 (SEQ ID NO:1). The 33 amino acid sequence presented in SEQ ID NO:6 trimerizes spontaneously in solution. Fusion proteins comprising this 33 amino acid sequence are thus expected to form trimers or multimers spontaneously.

The construct is prepared by synthesizing oligonucleotides representing a leader sequence, and the 33 amino acid sequence described above, then ligating the final product to a DNA fragment encoding amino acids 34 through 223 of SEQ ID NO:1, prepared as described in Example 1.

The resulting ligation product in expression vector pDC409 was transfected into the monkey kidney cell line CV-1/EBNA (ATCC CRL 10478). pDC409 differs from pDC406 in that a Bgl II restriction site outside of the multiple cloning site has been deleted, making the Bgl II site within the multiple cloning site unique.

Once cells expressing the fusion construct are identified, large scale cultures of transfected cells are grown to accumulate supernatant from cells expressing trimeric BZLF2. The trimeric BZLF2 fusion protein in supernatant fluid is purified by conventional protein purification methods; silver-stained SDS gels of the eluted BZLF2 fusion protein can be prepared to determine purity.

EXAMPLE 4

This example describes construction of a BZLF2 DNA construct to express a soluble BZLF2 fusion protein referred to as dimeric BZLF2. Dimeric BZLF2 contains a leader sequence, and a 33 amino acid sequence referred to as an "oligomerizing zipper" (SEQ ID NO:7), followed by the extracellular region of BZLF2 from amino acid 34 to amino acid 223 (SEQ ID NO:1). The 33 amino acid sequence presented in SEQ ID NO:7 is derived from the yeast GCN4 leucine zipper sequence (O'Shea et al., *Science* 243:538, 1989; Harbury et al., *Science* 262:1401, 1993), and forms a homodimer. Fusion proteins comprising this 33 amino acid sequence are thus expected to form homodimers spontaneously. The construct is prepared by synthesizing oligonucleotides representing a leader sequence, and the 33 amino acid sequence described above, then ligating the final product to a DNA fragment encoding amino acids 34 through 29 of SEQ ID NO:1, prepared as described in Example 1.

The resulting ligation product in a suitable expression vector (for example, pDC406) is transfected into the monkey kidney cell line CV-1/EBNA (ATCC CRL 10478). The pDC406 plasmid includes regulatory sequences derived from SV40, human immunodeficiency virus (HIV), and Epstein-Barr virus (EBV). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replication.

Once cells expressing the fusion construct are identified, large scale cultures of transfected cells are grown to accumulate supernatant from cells expressing dimeric BZLF2. The dimeric BZLF2 fusion protein in supernatant fluid is purified by using conventional protein purification methods, for example by one ore more steps utilizing ion exchange chromatography, size exclusion chromatography, or chromatography using hydrophobic interaction as a purification means. Affinity chromatography, for example using an antibody to BZLF2 or an antibody to the oligomerizing zipper sequence, are also useful, as is reverse-phase HPLC. Silver-stained SDS gels of the dimeric BZLF2 fusion protein can be prepared to determine purity.

EXAMPLE 5

This example describes construction of a BZLF2 DNA construct to express a soluble BZLF2 protein referred to as monomeric BZLF2. Monomeric BZLF2 contains a leader sequence, and the extracellular region of BZLF2 from amino acid 34 to amino acid 223 (SEQ ID NO:1). The construct is prepared essentially as described for other soluble constructs, by ligating a DNA fragment encoding amino acids 34 through 223 of SEQ ID NO:1 (prepared as described in Example 1) into an appropriate expression vector which contains a suitable leader sequence. The resultant DNA construct is transfected into a suitable cell line such as the monkey kidney cell line CV-1/EBNA (ATCC CRL 10478). Monomeric BZLF2 may be purified and analyzed using any of the methods described herein.

EXAMPLE 6

This example describes construction of a BZLF2 DNA construct to express a full length BZLF2. A PCR technique (Saiki et al., *Science* 239:487, 1988) was employed using 5' (upstream) and 3' (downstream) oligonucleotide primers to amplify the DNA sequences encoding BZLF2 extracellular ligand binding domain from a cosmid containing the portion of Epstein-Barr virus genome that encompasses the Bam HI Z fragment (*J. Virol.* 67:7298; 1993) which contains the BZLF2 ORF, to form a PCR fragment. The upstream oligonucleotide primer introduced a Sal 1 site upstream from the initiation codon of BZLF2; the downstream oligonucleotide primer introduced a Not 1 site just downstream of the termination codon of the BZLF2. The resulting PCR fragment was then ligated into an expression vector cut with Sal I/Not I. The resultant DNA construct (flBZLF2) is transfected into a suitable cell line such as the monkey kidney cell line CV-1/EBNA (ATCC CRL 10478), and is purified and analyzed using any of the methods described herein.

EXAMPLE 7

This example describes purification of BZLF2 fusion proteins. BZLF2/Fc fusion protein is purified by conventional methods using Protein A or Protein G chromatography. Approximately one liter of culture supernatant containing BZLF2/Fc fusion protein is purified by filtering mammalian cell supernatants (e.g., in a 0.45 m filter) and applying filtrate to a protein A/G antibody affinity column (Schleicher and Schuell, Keene, N. H.) at 4° C. at a flow rate of 80 ml/hr for a 1.5 cm×12.0 cm column. The column is washed with 0.5M NaCl in PBS until free protein is not detected in the wash buffer. Finally, the column is washed with PBS. Bound fusion protein is eluted from the column with 25 mM citrate buffer, pH 2.8, and brought to pH 7 with 500 mM Hepes buffer, pH 9.1.

A BZLF2 fusion protein comprising Flag® may also be detected and/or purified using an antibody that binds Flag®, substantially as described in Hopp et al., *Bio/Technology* 6:1204 (1988). Moreover, a BZLF2 protein comprising a poly-His peptide may be detected and/or purified using a poly-His system, substantially as described in U.S. Pat. No. 5,284,933, issued Feb. 8, 1994.

MHC Class II binding is used as an assay for detection of BZLF2 activity. Biological activity is measured in any biological assay which quantifies an antigen-specific immune response, for example, as described in Examples 9 through 12 herein.

EXAMPLE 8

This example illustrates the preparation of monoclonal antibodies against BZLF2. Preparations of purified recombinant BZLF2,for example, or transfected cells expressing high levels of BZLF2, are employed to generate monoclonal antibodies against BZLF2 using conventional techniques, such as those disclosed in U.S. Pat. No. 4,411,993. Such antibodies are likely to be useful in interfering with BZLF2 binding to MHC Class II antigens, as components of diagnostic or research assays for BZLF2, or in affinity purification of BZLF2.

To immunize rodents, BZLF2 immunogen is emulsified in an adjuvant (such as complete or incomplete Freund's adjuvant, alum, or another adjuvant, such as Ribi adjuvant R700 (Ribi, Hamilton, MT), and injected in amounts ranging from 10–100 μg subcutaneously into a selected rodent, for example, Balb/c mice or Lewis rats. Ten days to three weeks days later, the immunized animals are boosted with additional immunogen and periodically boosted thereafter on a weekly, biweekly or every third week immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable, for example, FACS analysis using cells expressing membrane-bound BZLF2. Following detection of an appropriate antibody titer, positive animals are given an intravenous injection of antigen in saline. Three to four days later, the animals are sacrificed, splenocytes harvested, and fused to a murine myeloma cell line (e.g., NSI or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with BZLF2, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mglml) of anti-BZLF2 monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to BZLF2 protein.

EXAMPLE 9

This example illustrates the ability of BZLF2/Fc to inhibit antigen-specific antibody formation. Human peripheral blood mononuclear cells (PBMCs) were purified from blood obtained from normal donors, by density gradient centrifugation over Histopaque® (Sigma, St. Louis, Mo.). Antigen-specific antibody formation was measured by a procedure substantially similar to that described in Grabstein et al., *J. Mol. Cell. Immunol.* 2:199, 1986. Briefly, purified PBMCs (2.0 ml cultures of $2\times10^6$ PBMCs per culture) were cultured in RPMI, pooled human AB serum (10%), in the presence of 0.03% v/v sheep erythrocytes for seven days, in the presence of BZLF2 /FC or a control Fc protein (Tie/Fc). Results are shown in Table 1.

TABLE 1

Inhibition of Production of Anti-SRBC Antibodies by BZLF2/Fc

| Addition | Plaques/$10^6$ PBMC |
|---|---|
| Medium | 0 |
| IL − 2 | 0 |
| IL2 + IL − 3 + IL − 10 | 904 |
| IL2 + IL − 3 + IL − 10 + | |
| Tie/Fc 20 μg/ml | 606 |
| Tie/Fc 10 μg/ml | 100 |
| Tie/Fc 4 μg/ml | 324 |
| Tie/Fc 2.5 μg/ml | 1228 |
| Tie/Fc 1.25 μg/ml | 692 |

TABLE 1-continued

Inhibition of Production of
Anti-SRBC Antibodies by BZLF2/Fc

| Addition | Plaques/10⁶ PBMC |
| --- | --- |
| IL2 + IL – 3 + IL – 10 + | |
| BZLF2/Fc 20 µg/ml | 0 |
| BZLF2/Fc 10 µg/ml | 0 |
| BZLF2/Fc  4 µg/ml | 0 |
| BZLF2/Fc  2.5 µg/ml | 0 |
| BZLF2/Fc  1.25 µg/ml | 0 |

A similar hemolytic plaque assay was performed with cells obtained from a second donor; the results are shown in Table 2. The control Fc fusion protein used in this experiment was an IL-4 receptor/Fc (IL-4R/Fc) fusion protein.

TABLE 2

Inhibition of Production of
Anti-SRBC Antibodies by BZLF2/Fc

| Addition | Plaques/10⁶ PBMC |
| --- | --- |
| None | 0 |
| IL – 2 | 43 |
| IL2 + IL – 3 + IL – 10 | 655 |
| IL2 + IL – 3 + IL – 10 + | |
| IL – 4R/Fc 300 ng/ml | 788 |
| IL – 4R/Fc 100 ng/ml | 564 |
| IL – 4R/Fc  30 ng/ml | 572 |
| IL2 + IL – 3 + IL – 10 + | |
| BZLF2/Fc 300 ng/ml | 0 |
| BZLF2/Fc 100 ng/ml | 51 |
| BZLF2/Fc  30 ng/ml | 326 |

These results indicate that BZLF2/Fc successfully inhibited the production of anti-SRBC antibodies. An ELISA was used to confirm that the antibodies produced were IgM.

EXAMPLE 10

Figure 2B:
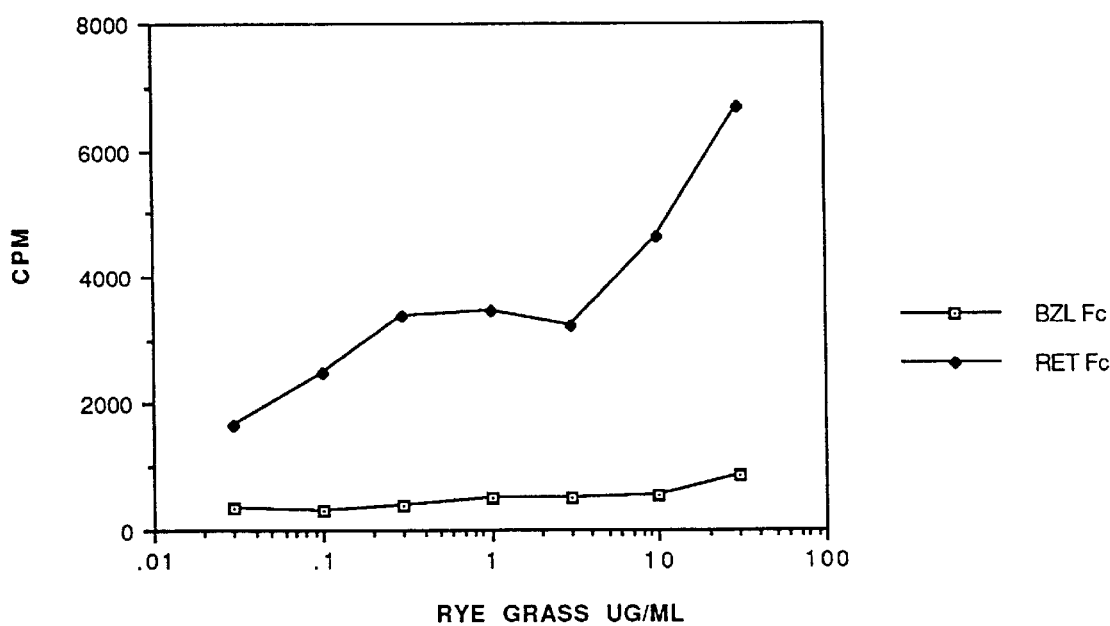

This example illustrates the ability of BZLF2/Fc to inhibit antigen-specific proliferation of peripheral blood mononuclear cells (PBMCs). PBMCs were obtained from the blood of a donor known to be allergic to rye grass, by density gradient centrifugation over Histopaque® (Sigma, St. Louis, Mo.). Cell proliferation assays were conducted with PBMCs in RPMI with added 10% heat-inactivated fetal bovine serum (FBS) in the presence of a titration of partially purified Lolium perenne antigen from perennial rye grass (Greer Labs Inc., Lenoir, N.C.), at 37° C. in a 10% $CO_2$ atmosphere. Approximately 1×10⁵ cells per well were cultured in triplicate in round-bottomed 96-well microtiter plates (Corning) for 7 days, in the presence of 10 µg/ml BZLF2/Fc or a control Fc protein (RET/Fc), in the presence or absence of IL-2 at 10 ng/ml. The cells were pulsed with 1 µCi/well of tritiated thymidine (25 Ci/nmole Amersham, Arlington Heights, Il.) for the final eight hours of culture. Cells were harvested onto glass fiber discs with an automated cell harvester and incorporated cpm were measured by liquid scintillation spectrometry. Results are shown in FIG. 2. These results demonstrated that BZLF2/Fc was able to inhibit a secondary, antigen-specific antibody response.

EXAMPLE 11

Figure 3A:
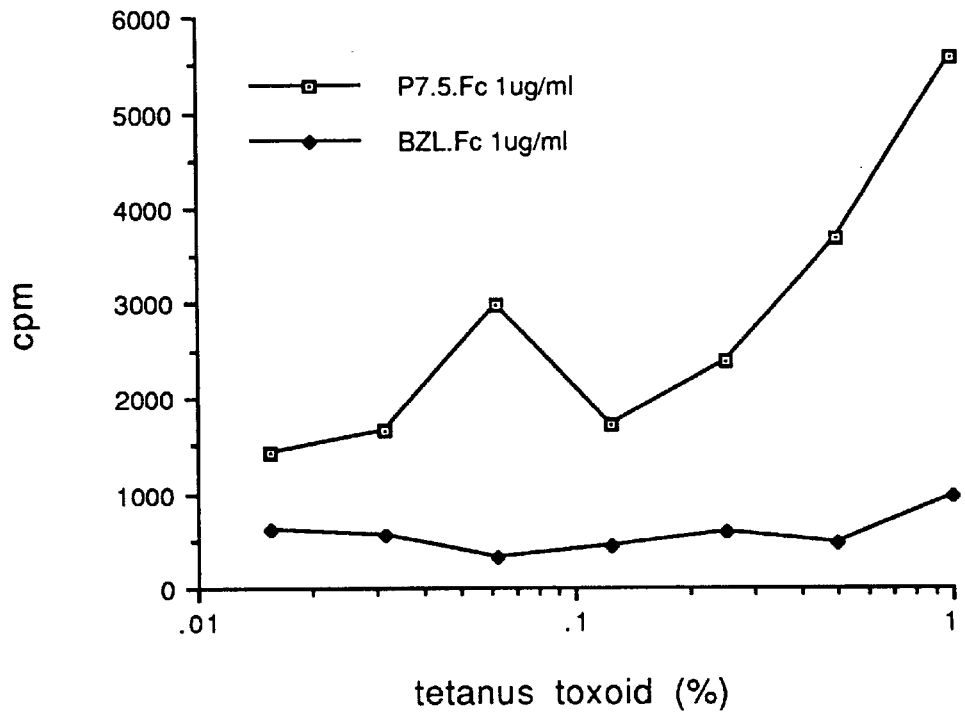
FIGS. 3A–3C confirms that BZLF2 is able to inhibit antigen-specific antibody formation. BZLF2/Fc was able to inhibit a secondary, antigen-specific antibody response in PBMCs from three individuals known to be reactive against tetanus toxoid. Results are presented for each individual in FIGS. 3A, 3B, and 3C.
Figure 3B:
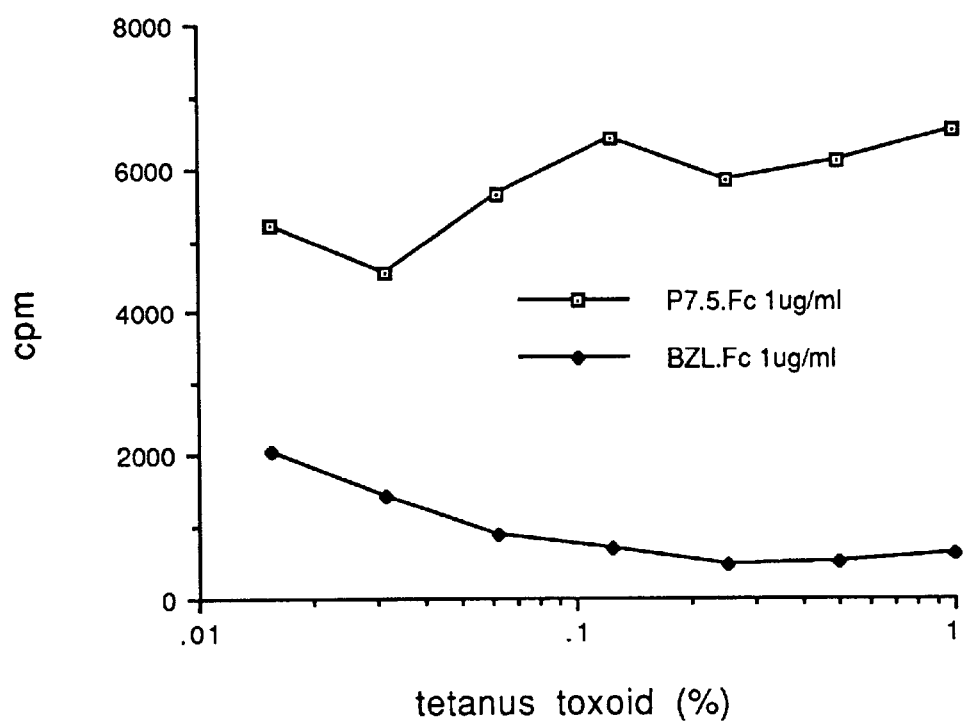
Figure 3C:
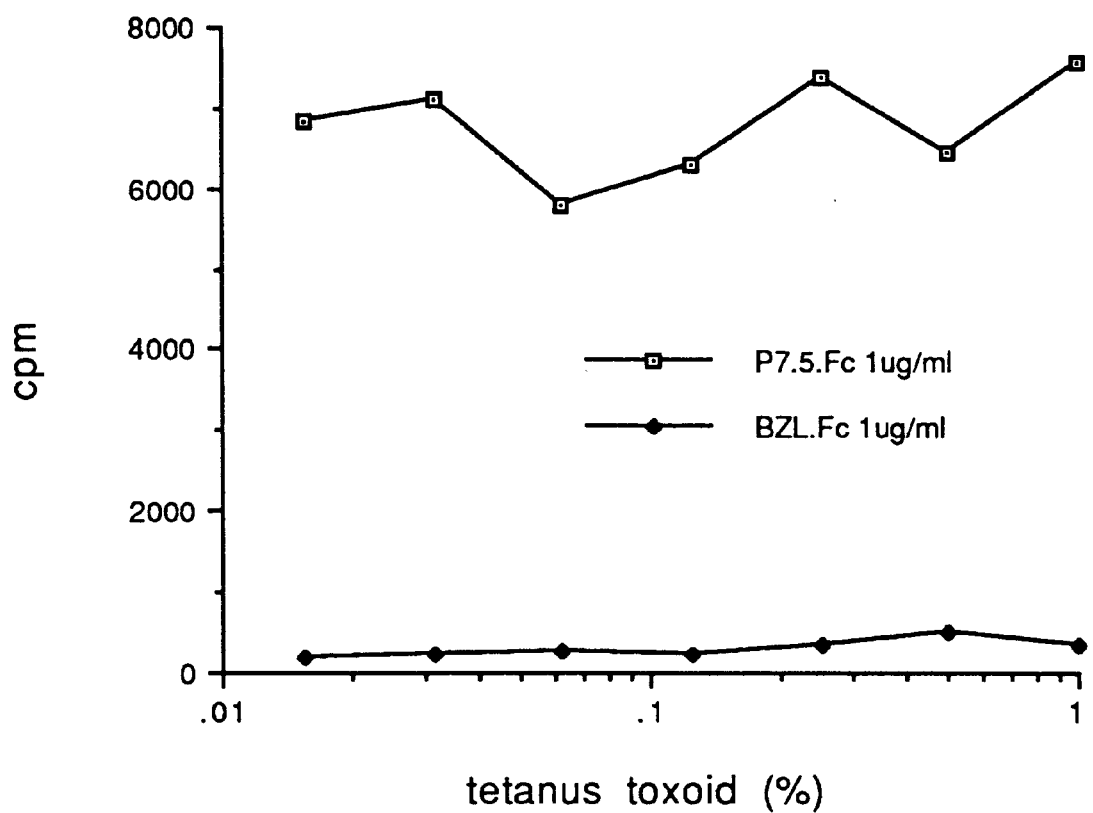
Figure 4A:
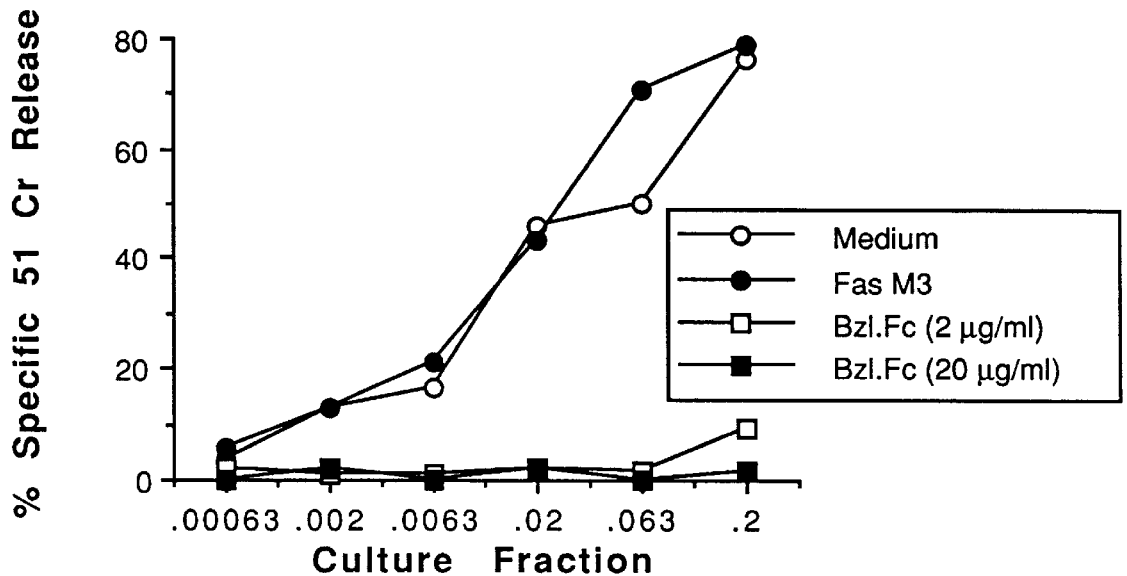
FIGS. 4A–4D demonstrates the ability of BZLF2 proteins to inhibit antigen-specific CTL generation.
Figure 4B:
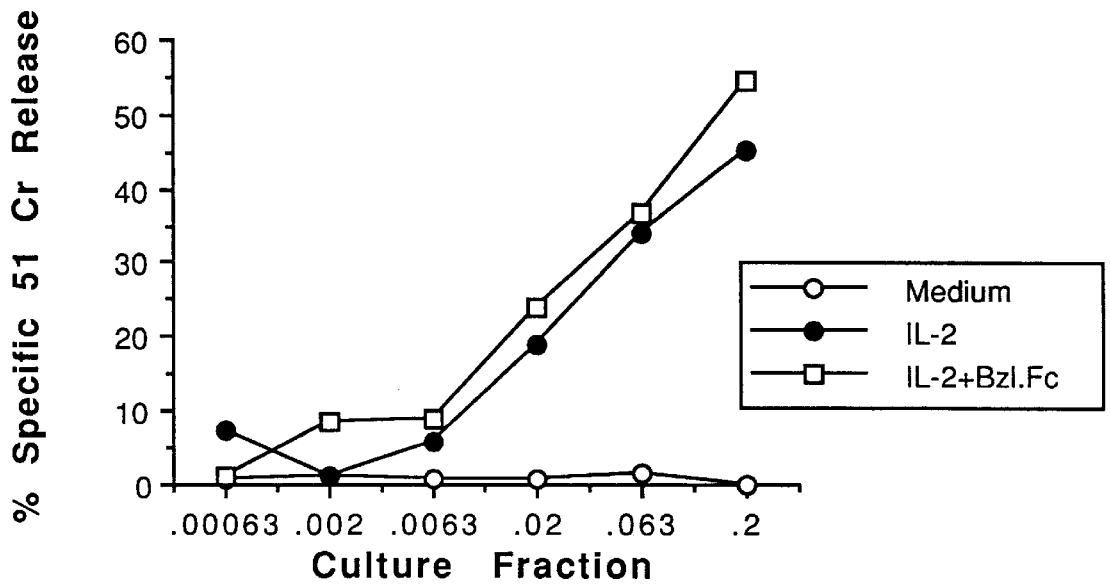
Figure 4C:
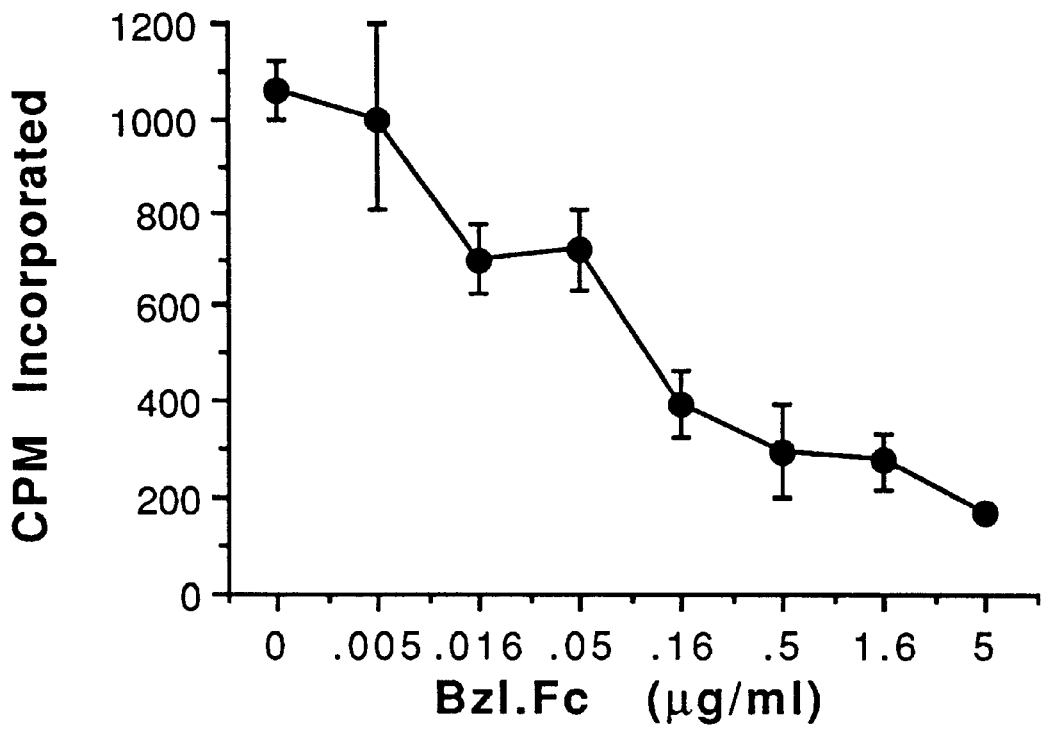
Figure 4D:
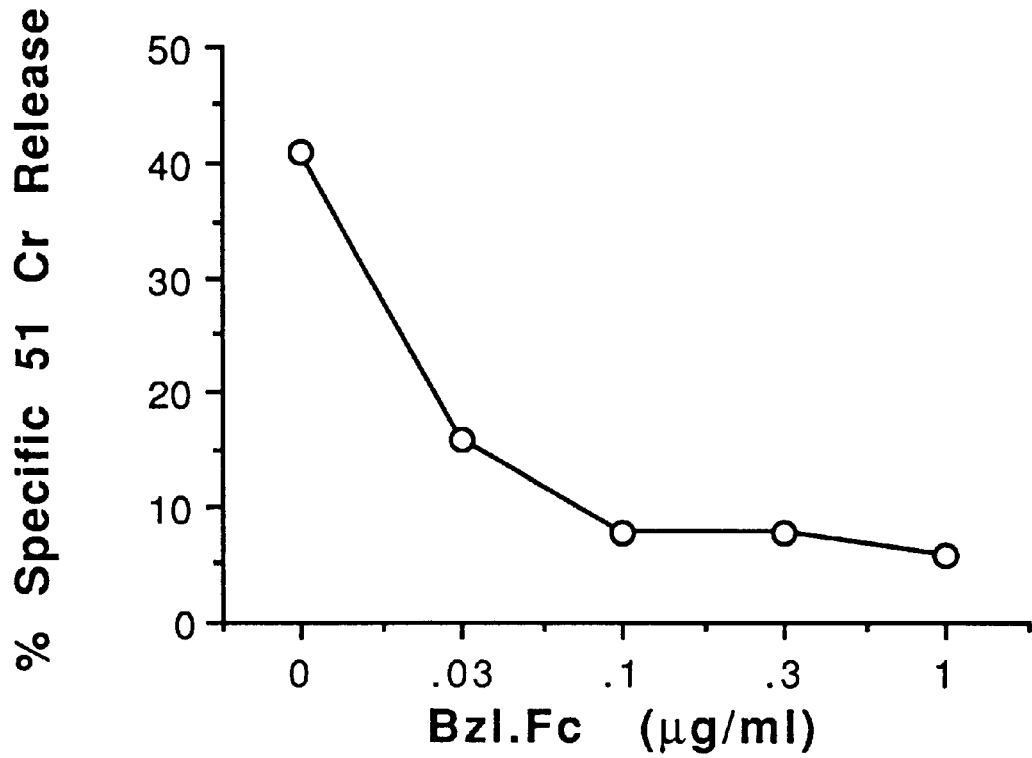

This example illustrates the ability of BZLF2/Fc to inhibit antigen-specific proliferation of peripheral blood mononuclear cells (PBMCs). PBMCs were obtained from three blood donors known to be reactive against tetanus toxoid, by density gradient centrifugation over Histopaque® (Sigma, St. Louis, Mo.). Cell proliferation assays were conducted with PBMCs in RPMI with added 10% heat-inactivated fetal bovine serum (FBS) at 37° C. in a 10% $CO_2$ atmosphere. Approximately 1×10⁵ cells per well were cultured in triplicate in round-bottomed 96-well microtiter plates (Corning) for 7 days, in the presence of 1 µg/ml BZLF2/Fc or a control Fc protein (7.5/Fc). The cells were pulsed with 1 µCi/well of tritiated thymidine (25 Ci/nmole, Amersham, Arlington Heights, Ill. for the final eight hours of culture. Cells were harvested onto glass fiber discs with an automated cell harvester and incorporated cpm were measured by liquid scintillation spectrometry. The results, which are shown in FIG. 3, confirmed that BZLF2/Fc inhibited a secondary antigen-specific immune response.

EXAMPLE 12

This example illustrates the ability of BZLF2/Fc to inhibit antigen-specific CTL generation. A 4-hour $^{51}Cr$ release assay was used to assess the cytolytic activity of human T cells essentially as described in Alderson et al., J. Exp. Med. 172:577 (1990). Briefly, freshly isolated peripheral blood mononuclear cells from one donor were cultured in MLC (mixed lymphocyte culture) with irradiated, allogeneic stimulating cells (target cells) from a second donor, either in the presence or absence of BZLF2 IFc at either 2 or 20 µg/ml, or a control protein, the anti-Fas antibody M3 (20 µg/ml; U.S. Ser. No. 08/159,003, filed Nov. 29, 1993). ⁵ICr-labeled target cells were prepared by incubating PHA-stimulated cells from the second donor with 100 µCi of 51 Cr for one hour at 37° C. Cell cultures to be assessed for cytolytic activity were washed twice in culture medium and serially diluted in 96-well V-bottom plates (Costar). $^{51}$ICr-labeled target cells (2×10³) were added to each well (total volume of 200 µl/well), and the plates were incubated for four hours at 37° C. After incubation, the plates were centrifuged at 150 g for five minutes, and harvested using a Skatron SCS harvesting system (Skatron, Sterling, Va.). $^{51}Cr$ content of the supernatants was determined using a Micromedic ME Plus gamma scintillation counter (Micromedic, Huntsville, Tenn.). Percent specific $^{51}Cr$ release was calculated according to the formula 100×(experimental cpm—spontaneous cpm)/(maximum cpm/spontaneous cpm) where spontaneous cpm=cpm released in the absence of effector cells and maximum cpm=cpm released in the presence of 1N HCl. Results are shown in FIG. 4. These results show that BZLF2/Fc completely inhibits the generation of cytolytic T lymphocytes in MLC, at concentrations as low as 2 µg/ml. The addition of IL-2 to the cultures reversed the inhibitory effect of BZLF2/Fc, confirming that BZLF2 was likely to be functioning through Class II (as opposed to Class I) in this system. Titrations of BZLF2 1Fc showed demonstrable inhibitory activity at very low concentrations.

EXAMPLE 13

Figure 5:
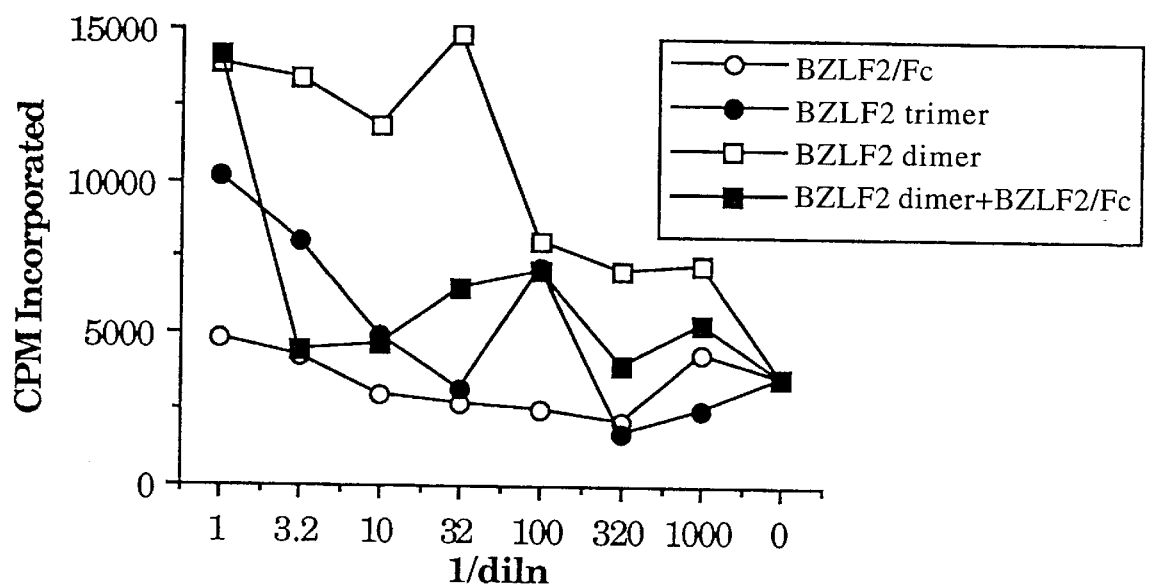
FIG. 5 illustrates the ability of certain soluble forms of BZLF2 to stimulate the proliferation of PBMCs. The results demonstrated that fusion proteins comprising the extracellular region of BZLF2 and either a dimer forming oligomerizing zipper or a trimerforming zipper domain stimulated proliferation of PBMCs, whereas BZLF2/Fc did not. BZLF2/Fc was also able to inhibit the proliferation induced by the other BZLF2 fusion proteins.

This example illustrates the ability of BZLF2 to stimulate PBMC proliferation without the requirement for antigen processing. Soluble BZLF2 constructs comprising the extracellular region of BZLF2 and either a dimeric oligomerizing zipper or a trimer-forming zipper moiety were prepared as described previously (referred to as BZLF2 dimer and BZLF2 trimer, respectively), and tested for the ability to induce proliferation of normal human PBMCs. PBMCs are isolated from a healthy donor by centrifugation of heparinized blood over Isolymph and washed three times with culture medium. Culture medium consists of RPMI 1640 supplemented with 10% FCS, 50 U/ml penicillin, 50 μg/ml streptomycin, 2 mM glutamine and $5 \times 10^{-5}$ M 2-ME. PBMCs ($4 \times 10^5$/well) are stimulated with either soluble BZLF2 transfected supernatant or control supernatant in culture medium in 96-well plates. After 5 days at 37° C., 1 μCi/well of [$^3$H] thymidine (Amersham Chemical Corp., Arlington Heights, Ill. is added for 16 hours. Results from a representative experiment are shown in FIG. 5. In contrast to control supernatants from cells transfected with vector only, supernatants containing either BZLF2 dimer or BZLF2 trimer induced proliferation of PBMCs in a dose dependent manner. BZLF2/Fc did not induce proliferation, and in fact appeared to inhibit proliferation induced by BZLF2 dimer. Therefore, the BZLF2 protein has superantigen-like activity.

EXAMPLE 14

This example illustrates the ability of BZLF2/Fc to inhibit transformation of human peripheral blood lymphocytes by EBV. Human leukocytes were obtained from heparinized adult peripheral blood by flotation on lymphocyte separation medium (Organon Teknika, West Chester, Pa.). T cells were depleted by a double cycle of rosetting with 2-aminoethylisothiouronium bromide-treated sheep erythrocytes and centrifugation on 60% Percoll (Pharmacia Fine Chemicals, Piscataway, N.J.).

Epstein-Barr virus (Akata strain) was obtained from Akata cells which were resuspended at a concentration of $4 \times 10^6$ cells per ml and induced with 100 μg anti-human immunoglobulin G per ml for 4 days. Spent culture medium was clarified by low speed centrifugation, passed through a 1.2 μm filter and stored at −80° C. as stock virus. Antibody F-2-1 (Strnad et al., *J. Virol.* 41:258-264, 1982) which reacts with the BZLF2 gene product, gp42, (Li et al., *J. Virol.* 69: in press (July issue), 1995 [Li et al. I]; Li et al., in *Epstein-Barr Virus and Associated Diseases*, Abstracts of papers presented at the Cold Spring Harbor Meeting on Cancer Cells, September 1994; Pagano and Rickinson, eds.; page 248 [Li et al. II]) was obtained from spent culture medium of hybridoma cells grown in RPMI 1640 supplemented with 20% heat inactivated fetal bovine serum (Hyclone) and purified by chromatography on protein A (Sigma) coupled to Affigel-15 (BioRad, Richmond, Calif.). Antibody F-2-1 neutralizes the ability of EBV to transform human B cells (Li et al. I).

T depleted human leukocytes were incubated for 30 minutes at 37° C. with 120 μl of RPMI 1640 alone or the same volume of medium containing BZLF2. Fc or a control protein (p7.5-2-Fc). An equal volume of virus at a 1/250 dilution from stock was added for another 30 minute incubation after which the total volume was increased with RPMI containing 10% fetal calf serum and the cells were plated out in 96 well plates at a concentration of 105 cells per well. A second set of cells was added to virus that had been preincubated for 30 minutes with 12 μg antibody F-2-1 in RPMI or the same volume of RPMI without antibody. These cells were also plated at a concentration of 105 cells per well. Cells were fed every five days and the number of transforming foci per well was evaluated at four weeks. Transformation was scored as follows: −, no transformation; +/−, some cell clumping, but no well-defined foci of cells; 1+, 5–10 small foci; 2+, 10–15 foci; 3+, 30–40 foci; 4+, >40 foci. Results are shown in Table 3 below.

TABLE 3

Effect of BZLF2/Fc on Ability of Akata Virus to Transform Human Peripheral Blood Lymphocytes

| | Addition[a] | Transforming foci per well | | | | |
|---|---|---|---|---|---|---|
| Experiment 1 | 0.14 μg BZLF2/Fc | − | − | − | − | − |
| | 1.4 μg BZLF2/Fc | − | − | − | − | +/− |
| | Medium | 3+ | 3+ | 3+ | 3+ | 3+ |
| | Antibody F-2-1 | − | − | − | − | − |
| Experiment 2 | 0.14 μg BZLF2/Fc | − | − | +/− | +/− | nd[b] |
| | 1.4 μg BZLF2/Fc | − | − | − | − | nd |
| | 0.14 μg Control/Fc | 2+ | 4+ | 3+ | 3+ | nd |
| | 1.4 μg Control/Fc | +/− | 3+ | 1+ | 1+ | nd |
| | Medium | 3+ | 3+ | 3+ | 4+ | nd |
| | Antibody F-2-1 | 1+ | − | − | − | nd |

[a]: Amount of protein per well
[b]: not done

These results demonstrate that BZLF2/Fc is able to inhibit the transformation of human peripheral blood lymphocytes by Epstein-Barr virus. Based on these results, and similar results that indicate BZLF2 proteins can inhibit infection of epithelial cells (see below), BZLF2 is directly antagonistic for EBV infection and transformation. BZLF2 proteins will also be useful for stimulating an anti-EBV immune response (for example, as a component of a vaccine).

EXAMPLE 15

This example illustrates the ability of BZLF2/Fc to inhibit infection of SVKCR2 cells by EBV. SVKCR2 cells (Li et al., *Nature* 356:347–350, 1992) were grown in Joklik's Modified DMEM (Gibco BRL, Life Technologies Inc., Grand Island, N.Y.) supplemented with 10% heat inactivated fetal bovine serum (Hyclone, Logan, UT) and 10 ng cholera toxin (Sigma Chemical Co., St. Louis, Mo.) per ml. Akata cells (Takada et al., *Int. J. Cancer* 33:27-32, 1984) were grown in RPMI 1640 (Sigma) supplemented with 10% heat inactivated fetal bovine serum (Gibco). Antibody ElDl (Oba et al., *J. Virol.* 62:1108–1114, 1988) was obtained from spent culture medium of hybridoma cells grown in RPMI 1640 supplemented with 20% heat inactivated fetal bovine serum (Hyclone) and purified by chromatography on protein A (Sigma) coupled to Affigel-15 (BioRad, Richmond, Calif.). This antibody reacts with an epitope dependent on coexpression of the EBV BXLF2 gene product, gp85, and the BKRF2 gene product, gp25, and neutralizes the ability of EBV to infect SVKCR2 cells and induce expression of Epstein-Barr virus nuclear antigen, EBNA (Li et al. I).

For Experiments 1 and 3, SVKCR2 cells were grown to 80% confluency in 10 cm dishes (approximately $3 \times 10^7$ cells per dish), washed with PBS, pH 7.2, and incubated for 90 minutes at 37° C. with 400 μl Joklik's medium alone, or with medium containing the indicated concentration of BZLF2. Fc or a control protein (B 18.R.2Fc). One ml virus was added directly to the treated cells, or preincubated for 90 minutes at 37° C. with 400 μg EIDI antibody in PBS or with the same volume of PBS without antibody. Plates were incubated overnight at 37° C. and 5 ml of Joklik's medium containing 10% heat inactivated fetal bovine serum were added to each. On day three, cells were removed from the plates by with trypsin, allowed to recover for 30 minutes in growth medium and fixed and stained for expression of EBNA as described below.

For Experiment 2, SVKCR2 cells were grown to 80% confluency in 38 mim dishes (6 well plates, approximately 5 10$^6$ cells), washed in PBS and incubated for 40 minutes at 37° C. with 400 μl Joklik's medium alone, or with medium containing the indicated concentration of BZLF2. Fc or a control protein (p7.5-2-Fc). Three hundred μl of virus was added directly to the treated cells, or preincubated for 90 minutes at 37° C. with 200 μg E1D1 antibody in PBS or with the same volume of PBS without antibody. Plates were incubated overnight at 37° C. and 2 ml Joklik's medium containing 10% heat inactivated fetal bovine serum was added to each. On day three cells were examined for EBNA expression as described below.

One hundred thousand SVKCR2 cells were air dried on a glass slide, fixed for 10 minutes in ice cold acetone:methanol 1:11 and reacted sequentially for 1 hour each with EBV seropositive human serum, seronegative human serum as a source of complement, and fluorescein conjugated goat anti-human C3 (Organon Teknika). A second sample of cells was reacted only with seronegative serum as a control. Cells were counterstained for 5 minutes in 0.01% Evans Blue (Sigma). Stained cells were mounted in 50% glycerol (v/v) in phosphate buffered saline (PBS), pH 8.6, containing 5% (w/v) 1,4-diazabicyclo-[2.2.]octane (DABCO (Sigma). The number of cells with fluorescent nuclear staining was counted under a fluorescent microscope. Results are shown in Table 4.

These results demonstrated that BZLF2/Fc was able to inhibit the infection of SVKCR2 cells by Epstein-Barr virus.

EXAMPLE 16

This example demonstrates that the region of BZLF2 that is important for binding to MHC class II β chain is the C-terminal region. Several deletion mutants of the BZLF2/Fc protein described above were prepared, deleting amino acids from either the N-terminus or the C-terminus. Several of the constructs took advantage of unique restriction enzyme sites to remove a segment of DNA encoding BZLF2. For other constructs, a PCR technique was employed to delete additional sections of DNA. Similar techniques can be used to prepare additional constructs. Ability to bind MHC class I μ chains was confirmed for two different clones of each deletion construct. Binding to MHC class II β chain was determined FACS staining and an autoradiographic slide binding assay, substantially as described herein. Binding was further confirmed by immunoprecipitation, using S. aureus protein A to precipitate BZLF2/Fc:MHC class II β chain complexes via binding to the Fc moiety. Results are shown in Table 5.

TABLE 4

Effect of BZLF2/Fc on Ability of Akata Virus to Infect SVKCR2 Cells

|  | Addition | Infected cells/ Uninfected Cells |
|---|---|---|
| Experiment 1 | PBS | 99/501 (19.8) |
|  | Antibody E1D1 | 2/500 (0.4) |
|  | 10 μg BZLF2/Fc | 5/500 (1.0) |
|  | 10 μg Control/Fc | 105/534 (19.7) |
| Experiment 2 | None[a] | 0 (0) |
|  | PBS | 54/321 (16.8) |
|  | Antibody E1D1 | 0 (0) |
|  | Joklik's medium | 51/323 (15.8) |
|  | 0.1 μg BZLF2/Fc | 47/281 (16.7) |
|  | 1.0 μg BZLF2/Fc | 18/290 (6.2) |
|  | 10 μg BZLF2/Fc | 4/221 (1.8) |
|  | 20 μg BZLF2/Fc | 1/244 (0.4) |
|  | 30 μg BZLF2/Fc | 1/401 (0.2) |
|  | 30 μg Control/Fc | 46/288 (16) |
| Experiment 3 | PBS | 175/644 (27.2) |
|  | Antibody E1D1 | 0 (0) |
|  | 1.0 μg BZLF2/Fc | 100/469 (21.3) |
|  | 10 μg BZLF2/Fc | 58/405 (14.3) |
|  | 30 μg BZLF2/Fc | 15/385 (3.9) |
|  | 15 μg Control/Fc | 107/448 (23.9) |

[a]: Negative control; no virus added

TABLE 5

Binding of MHC Class I β Chains by BZLF2 Deletion Mutants

| Type of Deletion | # Amino Acids Deleted | Location of Deletion[a] | Restriction Enzymes used | Expression level | MHC Binding |
|---|---|---|---|---|---|
| N-terminal | 25 | Pro60 | SpeI/HpaI | +++ | + |
| N-terminal | 57 | Pro91 | SpeI/PCR | +++ | + |
| N-terminal | 89 | His123 | SpeI/PCR | +++ | + |
| N-terminal | 121 | Asn155 | SpeI/BsmI | + | − |
| N-terminal | 156 | His191 | SpeI/NdeI | ++ | − |
| C-terminal | 28 | Val195 | NdeI/NotI | + | − |
| C-terminal | 63 | Glu160 | BsmI/NotI | + | − |
| C-terminal | 96 | Gly127 | PCR/NotI | ++ | − |
| C-terminal | 129 | Tyr94 | PCR/NotI | + | − |
| C-terminal | 160 | Phe63 | HpaI/NotI | +++ | − |

[a]: Location of deletion for N-terminal deletion mutants is the first (most N-terminal) amino acid from BZLF2 in the construct (i.e., NΔ25 consists of Pro60 through Ser223). Location of deletion for C-terminal deletion mutants is the last (most C-terminal) amino acid from BZLF2 in the construct (i.e., CΔ28 consists of Gly34 through Val195). The amino acid sequence is shown in SEQ ID NO: 1

These results confirm the importance of the C-terminal region (approximately the most C-terminal ⅔'s of the molecule) of BZLF2 for binding to MHC class II β chain as predicted from structural analysis of the amino acid sequence.

---

We claim:

1. An isolated fusion protein comprising a BZLF2 protein selected from the group consisting of a protein comprising amino acids 34 through 223 of SEQ ID NO:1, a protein comprising amino acids 60 through 223 of SEQ ID NO:1, a protein comprising amino acids 91 through 223 of SEQ ID NO:1, a protein comprising amino acids 123 through 223 of SEQ ID NO:1, and fragments thereof that bind MHC Class II β chain, and further comprising a domain selected from an immunoglobulin Fc region and an immunoglobulin Fc mutein.

2. The isolated fusion protein according to claim 1, wherein the immunoglobulin Fc comprises amino acids 1 through 213 of SEQ ID NO:4.

3. An isolated fusion protein comprising a BZLF2 protein selected from the group consisting of a protein comprising amino acids 34 through 223 of SEQ ID NO:1, a protein comprising amino acids 60 through 223 of SEQ ID NO:1, a protein comprising amino acids 91 through 223 of SEQ ID NO:1, a protein comprising amino acids 123 through 223 of SEQ ID NO:1, and fragments thereof that bind MHC Class II β chain, and further comprises an oligomerizing zipper domain.

4. The isolated BZLF2 fusion protein according to claim 3, wherein the oligomerizing zipper domain is selected from the group consisting of amino acids 1 through 33 of SEQ ID NO:6 and amino acids 1 through 33 of SEQ ID NO:7.

5. A composition comprising a BZLF2 fusion protein according to claim 2, and a suitable diluent or carrier.

6. A composition comprising a BZLF2 fusion protein according to claim 4, and a suitable diluent or carrier.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 223 amino acids
        (B) TYPE: amino acid
        (D) TOPOLOGY: linear (ii) MOLECULE TYPE: protein (vi) ORIGINAL SOURCE:
            (A) ORGANISM: Epstein-Barr Virus (vii) IMMEDIATE SOURCE:
            (B) CLONE: BZLF2

(xi) SEQUENCE DESCRIPTION: SEQ ID NO:1:

Met Val Ser Phe Lys Gln Val Arg Val Pro Leu Phe Thr Ala Ile Ala
1               5                   10                  15

Leu Val Ile Val Leu Leu Ala Tyr Phe Leu Pro Arg Val Arg
            20                  25                  30

Gly Gly Gly Arg Val Ala Ala Ala Ile Thr Trp Val Pro Lys Pro
            35                  40                  45

Asn Val Glu Val Trp Pro Val Asp Pro Pro Pro Val Asn Phe Asn
50                      55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                    85                  90                  95

Ala Asn Cys Thr Tyr Cys Asn Thr Arg Glu Tyr Thr Phe Ser Tyr Lys
                100                 105                 110

Gly Cys Cys Phe Tyr Phe Thr Lys Lys Lys His Thr Trp Asn Gly Cys
            115                 120                 125

Phe Gln Ala Cys Ala Glu Leu Tyr Pro Cys Thr Tyr Phe Tyr Gly Pro
        130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
                180                 185                 190

Thr Tyr Val Ser Lys Phe Ser Thr Val Pro Val Ser His His Glu Cys
            195                 200                 205

Ser Phe Leu Lys Pro Cys Leu Cys Val Ser Gln Arg Ser Asn Ser
210                 215                 220

(2) INFORMATION FOR SEQ ID NO:2:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (vi) ORIGINAL SOURCE:
            (A) ORGANISM: Mouse (vii) IMMEDIATE SOURCE:
            (B) CLONE: IL-7 signal peptide (xi) SEQUENCE DESCRIPTION: SEQ ID NO:2:

Met Phe His Val Ser Phe Arg Tyr Ile Phe Gly Ile Pro Pro Leu Ile
                5                   10                  15

Leu Val Leu Leu Pro Val Thr Ser Ser
            20                  25

(2) INFORMATION FOR SEQ ID NO:3:

(i) SEQUENCE CHARACTERISTICS:
            (A) LENGTH: 8 amino acids
            (B) TYPE: amino acid (D) TOPOLOGY: linear (ii) MOLECULE TYPE: peptide (vii) IMMEDIATE SOURCE:
         (B) CLONE: FLAG_ peptide (xi) SEQUENCE DESCRIPTION: SEQ ID NO:3:

Asp Tyr Lys Asp Asp Asp Asp Lys
 1               5

(2) INFORMATION FOR SEQ ID NO:4:

(i) SEQUENCE CHARACTERISTICS:
         (A) LENGTH: 212 amino acids
         (B) TYPE: amino acid
         (D) TOPOLOGY: linear (ii) MOLECULE TYPE: protein (vi) ORIGINAL SOURCE:
         (A) ORGANISM: Human (vii) IMMEDIATE SOURCE:
         (B) CLONE: IgG1 Fc (xi) SEQUENCE DESCRIPTION: SEQ ID NO:4:

Arg Ser Cys Asp Lys Thr His Thr Cys Pro Pro Cys Pro Ala Pro Glu
 1               5                  10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His
    210

(2) INFORMATION FOR SEQ ID NO:5:

(i) SEQUENCE CHARACTERISTICS:
         (A) LENGTH: 14 amino acids
         (B) TYPE: amino acid
         (D) TOPOLOGY: linear -continued

```
    (ii) MOLECULE TYPE: peptide (vii) IMMEDIATE SOURCE:
         (B) CLONE: Polylinker (xi) SEQUENCE DESCRIPTION: SEQ ID NO:5:

Gly Gly Gly Gly Ser Gly Gly Gly Ser Gly Gly Gly Gly
 1               5                  10

(2) INFORMATION FOR SEQ ID NO:6:

(i) SEQUENCE CHARACTERISTICS:
         (A) LENGTH: 33 amino acids
         (B) TYPE: amino acid
         (D) TOPOLOGY: linear (ii) MOLECULE TYPE: peptide (vii) IMMEDIATE SOURCE:
         (B) CLONE: Trimeric Leucine Zipper (xi) SEQUENCE DESCRIPTION: SEQ ID NO:6:

Arg Met Lys Gln Ile Glu Asp Lys Ile Glu Glu Ile Leu Ser Lys Ile
 1               5                  10                  15

Tyr His Ile Glu Asn Glu Ile Ala Arg Ile Lys Lys Leu Ile Gly Glu
             20                  25                  30

Arg (2) INFORMATION FOR SEQ ID NO:7:

(i) SEQUENCE CHARACTERISTICS:
         (A) LENGTH: 33 amino acids
         (B) TYPE: amino acid
         (D) TOPOLOGY: linear (ii) MOLECULE TYPE: peptide (vii) IMMEDIATE SOURCE:
         (B) CLONE: Dimeric Leucine Zipper (xi) SEQUENCE DESCRIPTION: SEQ ID NO:7:

Arg Met Lys Gln Leu Glu Asp Lys Val Glu Glu Leu Leu Ser Lys Val
 1               5                  10                  15

Tyr His Leu Glu Asn Glu Val Ala Arg Leu Lys Lys Leu Val Gly Glu
             20                  25                  30

Arg
```